United States Patent
Uwer et al.

(12) 
(10) Patent No.: US 7,112,718 B2
(45) Date of Patent: Sep. 26, 2006

(54) TRANSGENIC PLANTS SYNTHESIZING HIGH AMYLOSE STARCH

(76) Inventors: Ursula Uwer, Hasenheide 49, 10967, Berlin (DE); Claus Frohberg, Apoldaer Strasse 14, 12249, Berlin (DE); Jens Pilling, Melchiorstrasse 36, 50670, Köln (DE); Volker Landschütze, Gardeschützenweg 51, 12203, Berlin (DE)

( * ) Notice: Subject to any disclaimer, the term of this patent is extended or adjusted under 35 U.S.C. 154(b) by 133 days.

(21) Appl. No.: 10/171,008

(22) Filed: Jun. 11, 2002

(65) Prior Publication Data

US 2003/0126633 A1    Jul. 3, 2003

(30) Foreign Application Priority Data

Jun. 12, 2001  (DE) .................. 101 28 363

(51) Int. Cl.
    *C12N 15/82*   (2006.01)
    *C12N 5/04*    (2006.01)
    *C12N 5/10*    (2006.01)
    *A01H 5/00*    (2006.01)
    *C12N 15/29*   (2006.01)
    *C12N 15/54*   (2006.01)
    *C12P 19/04*   (2006.01)

(52) U.S. Cl. ............... 800/284; 800/286; 800/317.2; 435/101; 435/194; 435/419; 435/468; 536/23.6; 536/24.5

(58) Field of Classification Search .......... 800/278, 800/284, 286, 317.2; 435/101, 194, 419, 435/468; 536/24.5
See application file for complete search history.

(56) References Cited

U.S. PATENT DOCUMENTS 6,207,880 B1   3/2001   Kossmann ............ 800/284

2001/0007155 A1   7/2001   Kossmann ............ 800/284

FOREIGN PATENT DOCUMENTS

| DE | 196 53 176 A1 | 6/1998 |
|---|---|---|
| WO | WO 97/11188 | 3/1997 |
| WO | WO 97/20040 | * 6/1997 |
| WO | WO 98/27212 | 6/1998 |

OTHER PUBLICATIONS

Kortstee et al. Portland Press Proceedings 14: 89-98 (1998).*
Duwenig et al. The Plant Journal 12(2): 323-333 (1997).*
Ritte et al. Starch 52(6-7): 179-185 (2000).*
Safford et al. Carbohydrate Polymers 35(3-4): 155-168 (1998).*
Kull et al. Journal of Genetics and Breeding 49(1): 69-76 (Mar. 1995).*
Kuipers et al. The Plant Cell 6(1): 43-52 (Jan. 1994).*
Glover & Mertz, "Chapter 7, Par. 4.1.2.1: Starch" and "Chapter 7, Par. 5.2.4.2: High Amylose Corn," in *Nutritional Quality of Cereal Grains: Genetic and Agronomic Improvement*, American Society of Agronomy, Olson & Frey eds., pp. 183, 201-202, 269-271 (1987).
Lorberth et al., "Inhibition of Starch-Granule-Bound Protein Leads to Modified Starch and Repression of Cold Sweetening," *Nature Biotech.* 16: 473-477 (1998).
Schwall et al., "Production of Very-High-Amylose Potato Starch by Inhibition of SBE A and B," *Nature Biotech.* 18: 551-554 (2000).
Shi et al., "Molecular Structure of a Low-Amylopectin Starch and Other High-Amylose Maize Starches," *J. Cereal Sci.* 27: 289-99 (1998).

* cited by examiner

*Primary Examiner*—David T. Fox
(74) *Attorney, Agent, or Firm*—Fish & Neave IP Group Ropes & Gray LLP

(57) ABSTRACT

Transgenic plant cells and plants are described which synthesize a starch which is modified in comparison with corresponding wild type plant cells and plants. The plant cells and plants described show a reduced activity of R1, BEI and BEII proteins. Furthermore, modified starches as well as methods for their production are described.

20 Claims, 4 Drawing Sheets

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

<400> SEQUENCE: 1
gggggtgttg gctttgacta                                           20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide

<400> SEQUENCE: 2

-continued

```
ccctcctcct cctaatccca                                               20

<210> SEQ ID NO 3
<211> LENGTH: 1255
<212> TYPE: DNA
<213> ORGANISM: Solanum tuberosum
<220> FEATURE:
<221> NAME/KEY: CDS
<222> LOCATION: (2)..(928)
<223> OTHER INFORMATION:

<400> SEQUENCE: 3 a ttt tgt att ccc gtt caa gat ggg ggt gtt ggc ttt gac tat cgg ctg    49
  Phe Cys Ile Pro Val Gln Asp Gly Gly Val Gly Phe Asp Tyr Arg Leu
   1               5                  10                  15 cat atg gca att gct gat aaa tgg att gag ttg ctc aag aaa cgg gat     97
His Met Ala Ile Ala Asp Lys Trp Ile Glu Leu Leu Lys Lys Arg Asp
             20                  25                  30 gag gat tgg aga gtg ggt gat att gtt cat aca ctg aca aat aga aga    145
Glu Asp Trp Arg Val Gly Asp Ile Val His Thr Leu Thr Asn Arg Arg
         35                  40                  45 tgg tcg gaa aag tgt gtt tca tac gct gaa agt cat gat caa gct cta    193
Trp Ser Glu Lys Cys Val Ser Tyr Ala Glu Ser His Asp Gln Ala Leu
     50                  55                  60 gtc ggt gat aaa act ata gca ttc tgg ctg atg gac aag gat atg tat    241
Val Gly Asp Lys Thr Ile Ala Phe Trp Leu Met Asp Lys Asp Met Tyr
 65                  70                  75                  80 gat ttt atg gct ttg gat aga ccg tca aca tca tta ata gat cgt ggg    289
Asp Phe Met Ala Leu Asp Arg Pro Ser Thr Ser Leu Ile Asp Arg Gly
                 85                  90                  95 ata gca ttg cac aag atg att agg ctt gta act atg gga tta gga gga    337
Ile Ala Leu His Lys Met Ile Arg Leu Val Thr Met Gly Leu Gly Gly
            100                 105                 110 gaa ggg tac cta aat ttc atg gga aat gaa ttc ggc cac cct gag tgg    385
Glu Gly Tyr Leu Asn Phe Met Gly Asn Glu Phe Gly His Pro Glu Trp
        115                 120                 125 att gat ttc cct agg gct gaa caa cac ctc tct gat ggc tca gta att    433
Ile Asp Phe Pro Arg Ala Glu Gln His Leu Ser Asp Gly Ser Val Ile
    130                 135                 140 ccc gga aac caa ttc agt tat gat aaa tgc aga cgg aga ttt gac ctg    481
Pro Gly Asn Gln Phe Ser Tyr Asp Lys Cys Arg Arg Arg Phe Asp Leu
145                 150                 155                 160 gga gat gca gaa tat tta aga tac cgt ggg ttg caa gaa ttt gac cgg    529
Gly Asp Ala Glu Tyr Leu Arg Tyr Arg Gly Leu Gln Glu Phe Asp Arg
                165                 170                 175 gct atg cag tat ctt gaa gat aaa tat gag ttt atg act tca gaa cac    577
Ala Met Gln Tyr Leu Glu Asp Lys Tyr Glu Phe Met Thr Ser Glu His
            180                 185                 190 cag ttc ata tca cga aag gat gaa gga gat agg atg att gta ttt gaa    625
Gln Phe Ile Ser Arg Lys Asp Glu Gly Asp Arg Met Ile Val Phe Glu
        195                 200                 205 aaa gga aac cta gtt ttt gtc ttt aat ttt cac tgg aca aaa agc tat    673
Lys Gly Asn Leu Val Phe Val Phe Asn Phe His Trp Thr Lys Ser Tyr
    210                 215                 220 tca gac tat cgc ata ggc tgc ctg aag cct gga aaa tac aag gtt gcc    721
Ser Asp Tyr Arg Ile Gly Cys Leu Lys Pro Gly Lys Tyr Lys Val Ala
225                 230                 235                 240 ttg gac tca gat gat cca ctt ttt ggt ggc ttc ggg aga att gat cat    769
Leu Asp Ser Asp Asp Pro Leu Phe Gly Gly Phe Gly Arg Ile Asp His
                245                 250                 255
```

```
aat gcc gaa tgt ttc acc ttt gaa gga tgg tat gat gat cgt cct cgt    817
Asn Ala Glu Cys Phe Thr Phe Glu Gly Trp Tyr Asp Asp Arg Pro Arg
        260                 265                 270 tca att atg gtg tat gca cct agt aga aca gca gtg gtc tat gca cta    865
Ser Ile Met Val Tyr Ala Pro Ser Arg Thr Ala Val Val Tyr Ala Leu
        275                 280                 285 gta gac aaa gaa gaa gaa gaa gaa gta gca gta gta gaa gaa gta        913
Val Asp Lys Glu Glu Glu Glu Glu Val Ala Val Val Glu Glu Val
        290                 295                 300 gta gta gaa gaa gaa tgaacgaact tgtgatcgcg ttgaaagatt tgaacgctac    968
Val Val Glu Glu Glu
305 atagagcttc ttgacgtatc tggcaatatt gcatcagtct ggcggaatt tcatgtgaca   1028 aaaggtttgc aattctttcc actattagta gtgcaacgat atacgcagag atgaagtgct  1088 gaacaaacat atgtaaaatc gatgaattta tgtcgaatgc tgggacgggc ttcagcaggt  1148 tttgcttagt gagttctgta aattgtcatc tctttatatg tacagccaac tagaaatcaa  1208 ttatgtgaga cctaaaatac aataaccata aaatggaaat agtgctg                1255

<210> SEQ ID NO 4
<211> LENGTH: 309
<212> TYPE: PRT
<213> ORGANISM: Solanum tuberosum

<400> SEQUENCE: 4

Phe Cys Ile Pro Val Gln Asp Gly Gly Val Gly Phe Asp Tyr Arg Leu
1               5                   10                  15

His Met Ala Ile Ala Asp Lys Trp Ile Glu Leu Leu Lys Lys Arg Asp
            20                  25                  30

Glu Asp Trp Arg Val Gly Asp Ile Val His Thr Leu Thr Asn Arg Arg
        35                  40                  45

Trp Ser Glu Lys Cys Val Ser Tyr Ala Glu Ser His Asp Gln Ala Leu
    50                  55                  60

Val Gly Asp Lys Thr Ile Ala Phe Trp Leu Met Asp Lys Asp Met Tyr
65                  70                  75                  80

Asp Phe Met Ala Leu Asp Arg Pro Ser Thr Ser Leu Ile Asp Arg Gly
                85                  90                  95

Ile Ala Leu His Lys Met Ile Arg Leu Val Thr Met Gly Leu Gly Gly
            100                 105                 110

Glu Gly Tyr Leu Asn Phe Met Gly Asn Glu Phe Gly His Pro Glu Trp
        115                 120                 125

Ile Asp Phe Pro Arg Ala Glu Gln His Leu Ser Asp Gly Ser Val Ile
    130                 135                 140

Pro Gly Asn Gln Phe Ser Tyr Asp Lys Cys Arg Arg Arg Phe Asp Leu
145                 150                 155                 160

Gly Asp Ala Glu Tyr Leu Arg Tyr Arg Gly Leu Gln Glu Phe Asp Arg
                165                 170                 175

Ala Met Gln Tyr Leu Glu Asp Lys Tyr Glu Phe Met Thr Ser Glu His
            180                 185                 190

Gln Phe Ile Ser Arg Lys Asp Glu Gly Asp Arg Met Ile Val Phe Glu
        195                 200                 205

Lys Gly Asn Leu Val Phe Val Phe Asn Phe His Trp Thr Lys Ser Tyr
    210                 215                 220

Ser Asp Tyr Arg Ile Gly Cys Leu Lys Pro Gly Lys Tyr Lys Val Ala
225                 230                 235                 240
```

-continued

```
Leu Asp Ser Asp Asp Pro Leu Phe Gly Gly Phe Gly Arg Ile Asp His
            245                 250                 255

Asn Ala Glu Cys Phe Thr Phe Glu Gly Trp Tyr Asp Arg Pro Arg
            260                 265                 270

Ser Ile Met Val Tyr Ala Pro Ser Arg Thr Ala Val Val Tyr Ala Leu
            275                 280                 285

Val Asp Lys Glu Glu Glu Glu Val Ala Val Val Glu Glu Val
    290                 295                 300

Val Val Glu Glu Glu
305
```

<210> SEQ ID NO 5
<211> LENGTH: 5061
<212> TYPE: DNA
<213> ORGANISM: Solanum tuberosum
<220> FEATURE:
<221> NAME/KEY: CDS
<222> LOCATION: (216)..(4607)
<223> OTHER INFORMATION:

<400> SEQUENCE: 5

```
gaattgtaat acgactcact atagggcgaa ttgggtaccg ggcccccct cgaggtcgac      60 ggtatcgata agcttgatat cgaattcgcg gccgcttttg cttcgtgaat tcatcttcat    120
cgaatttctc gacgcttctt cgctaatttc ctcgttactt cactagaaat cgacgtttct    180
agctgaactt gagtgaatta agccagtggg aggat atg agt aat tcc tta ggg        233
                                      Met Ser Asn Ser Leu Gly
                                        1               5 aat aac ttg ctg tac cag gga ttc cta acc tca aca gtg ttg gaa cat      281
Asn Asn Leu Leu Tyr Gln Gly Phe Leu Thr Ser Thr Val Leu Glu His
         10                  15                  20 aaa agt aga atc agt cct cct tgt gtt gga ggc aat tct ttg ttt caa      329
Lys Ser Arg Ile Ser Pro Pro Cys Val Gly Gly Asn Ser Leu Phe Gln
     25                  30                  35 caa caa gtg atc tcg aaa tca cct tta tca act gag ttt cga ggt aac      377
Gln Gln Val Ile Ser Lys Ser Pro Leu Ser Thr Glu Phe Arg Gly Asn
 40                  45                  50 agg tta aag gtg cag aaa aag aaa ata cct atg gga aag aac cgt gct      425
Arg Leu Lys Val Gln Lys Lys Lys Ile Pro Met Gly Lys Asn Arg Ala
55                  60                  65                  70 ttt tct agt tct cct cat gct gta ctt acc act gat acc tct tct gag      473
Phe Ser Ser Ser Pro His Ala Val Leu Thr Thr Asp Thr Ser Ser Glu
                 75                  80                  85 cta gca gaa aag ttc agt cta gaa ggg aat att gag cta cag gtt gat      521
Leu Ala Glu Lys Phe Ser Leu Glu Gly Asn Ile Glu Leu Gln Val Asp
             90                  95                 100 gtt agg cct ccc act tca ggt gat gtg tcc ttt gtg gat ttt caa gct      569
Val Arg Pro Pro Thr Ser Gly Asp Val Ser Phe Val Asp Phe Gln Ala
         105                 110                 115 aca aat ggt agt gat aaa ctg ttt ttg cac tgg ggg gca gta aag ttc      617
Thr Asn Gly Ser Asp Lys Leu Phe Leu His Trp Gly Ala Val Lys Phe
     120                 125                 130 gga aaa gaa aca tgg tct ctt cct aat gat cgt cca gat ggg acc aaa      665
Gly Lys Glu Thr Trp Ser Leu Pro Asn Asp Arg Pro Asp Gly Thr Lys
135                 140                 145                 150 gtg tac aag aac aaa gca ctt aga act cca ttt gtt aaa tct ggc tct      713
Val Tyr Lys Asn Lys Ala Leu Arg Thr Pro Phe Val Lys Ser Gly Ser
                 155                 160                 165 aac tcc atc ctg aga ctg gag ata cgg gac act gct atc gaa gct att      761
Asn Ser Ile Leu Arg Leu Glu Ile Arg Asp Thr Ala Ile Glu Ala Ile
```

-continued

| | | 170 | | | | 175 | | | | 180 | | | |
|---|---|---|---|---|---|---|---|---|---|---|---|---|---|
| gag | ttt | ctc | ata | tac | gat | gaa | gcc | tac | gat | aaa | tgg | ata | aag | aat | aat | 809 |
| Glu | Phe | Leu | Ile | Tyr | Asp | Glu | Ala | Tyr | Asp | Lys | Trp | Ile | Lys | Asn | Asn | |
| | | 185 | | | | 190 | | | | 195 | | | | | | | ggt ggc aat ttt cgt gtc aaa ttg tca aga aaa gag ata cga ggc cca    857
Gly Gly Asn Phe Arg Val Lys Leu Ser Arg Lys Glu Ile Arg Gly Pro
        200                 205                 210 gat gtt tca gtt cct gag gag ctt gta cag atc caa tca tat ttg agg    905
Asp Val Ser Val Pro Glu Glu Leu Val Gln Ile Gln Ser Tyr Leu Arg
215                 220                 225                 230 tgg gag agg aag gga aaa cag aat tac acc cct gag aaa gag aag gag    953
Trp Glu Arg Lys Gly Lys Gln Asn Tyr Thr Pro Glu Lys Glu Lys Glu
                235                 240                 245 gaa tat gag gct gct cga act gag cta cag gag gaa ata gct cgt ggt    1001
Glu Tyr Glu Ala Ala Arg Thr Glu Leu Gln Glu Glu Ile Ala Arg Gly
            250                 255                 260 gct tcc ata cag gac att cga gca agg cta aca aaa act aat gat aaa    1049
Ala Ser Ile Gln Asp Ile Arg Ala Arg Leu Thr Lys Thr Asn Asp Lys
        265                 270                 275 agt caa agc aaa gaa gag cct ctt cat gta aca aag agt gaa ata cct    1097
Ser Gln Ser Lys Glu Glu Pro Leu His Val Thr Lys Ser Glu Ile Pro
280                 285                 290 gat gac ctt gcc caa gca caa gct tac att agg tgg gag aaa gca gga    1145
Asp Asp Leu Ala Gln Ala Gln Ala Tyr Ile Arg Trp Glu Lys Ala Gly
295                 300                 305                 310 aag ccg aac tat cct cca gaa aag caa att gaa gaa ctc gaa gaa gca    1193
Lys Pro Asn Tyr Pro Pro Glu Lys Gln Ile Glu Glu Leu Glu Glu Ala
                315                 320                 325 aga aga gaa ttg caa ctt gag ctt gag aaa ggc att acc ctt gat gag    1241
Arg Arg Glu Leu Gln Leu Glu Leu Glu Lys Gly Ile Thr Leu Asp Glu
            330                 335                 340 ttg cgg aaa aag att aca aaa ggg gag ata aaa act aag gcg gaa aag    1289
Leu Arg Lys Lys Ile Thr Lys Gly Glu Ile Lys Thr Lys Ala Glu Lys
        345                 350                 355 cac gtg aaa aga agc tct ttt gcc gtt gaa aga atc caa aga aag aag    1337
His Val Lys Arg Ser Ser Phe Ala Val Glu Arg Ile Gln Arg Lys Lys
360                 365                 370 aga gac ttt ggg cag ctt att aat aag tat cct tcc agt cct gca gta    1385
Arg Asp Phe Gly Gln Leu Ile Asn Lys Tyr Pro Ser Ser Pro Ala Val
375                 380                 385                 390 caa gta caa aag gtc ttg gaa gaa cca cca gcc tta tct aaa att aag    1433
Gln Val Gln Lys Val Leu Glu Glu Pro Pro Ala Leu Ser Lys Ile Lys
                395                 400                 405 ctg tat gcc aag gag aag gag gag cag att gat gat ccg atc ctt aat    1481
Leu Tyr Ala Lys Glu Lys Glu Glu Gln Ile Asp Asp Pro Ile Leu Asn
            410                 415                 420 aaa aag atc ttt aag gtc gat gat ggg gag cta ctg gta ctg gta gca    1529
Lys Lys Ile Phe Lys Val Asp Asp Gly Glu Leu Leu Val Leu Val Ala
        425                 430                 435 aag tcc tct ggg aag aca aaa gta cat ata gct aca gat ctg aat cag    1577
Lys Ser Ser Gly Lys Thr Lys Val His Ile Ala Thr Asp Leu Asn Gln
440                 445                 450 cca att act ctt cac tgg gca tta tcc aaa agt cgt gga gag tgg atg    1625
Pro Ile Thr Leu His Trp Ala Leu Ser Lys Ser Arg Gly Glu Trp Met
455                 460                 465                 470 gta cca cct tca agc ata ttg cct cct gga tca att att tta gac aag    1673
Val Pro Pro Ser Ser Ile Leu Pro Pro Gly Ser Ile Ile Leu Asp Lys
                475                 480                 485 gct gcc gaa aca cct ttt tcc gcc agt tct tct gat ggt cta act tct    1721

```
                                                                              -continued Ala Ala Glu Thr Pro Phe Ser Ala Ser Ser Ser Asp Gly Leu Thr Ser
            490                 495                 500 aag gta caa tct ttg gat ata gta att gaa gat ggc aat ttt gtg ggg         1769
Lys Val Gln Ser Leu Asp Ile Val Ile Glu Asp Gly Asn Phe Val Gly
            505                 510                 515 atg cca ttt gtt ctt ttg tct ggt gaa aaa tgg att aag aac caa ggg         1817
Met Pro Phe Val Leu Leu Ser Gly Glu Lys Trp Ile Lys Asn Gln Gly
        520                 525                 530 tcg gat ttc tat gtt gac ttc agt gct gca tcc aaa tta gca ctc aag         1865
Ser Asp Phe Tyr Val Asp Phe Ser Ala Ala Ser Lys Leu Ala Leu Lys
535                 540                 545                 550 gct gct ggg gat ggc agt gga act gca aag tct tta ctg gat aaa ata         1913
Ala Ala Gly Asp Gly Ser Gly Thr Ala Lys Ser Leu Leu Asp Lys Ile
                        555                 560                 565 gca gat atg gaa agt gag gct cag aag tca ttt atg cac cgg ttt aat         1961
Ala Asp Met Glu Ser Glu Ala Gln Lys Ser Phe Met His Arg Phe Asn
                570                 575                 580 att gct gct gac ttg ata gaa gat gcc act agt gct ggt gaa ctt ggt         2009
Ile Ala Ala Asp Leu Ile Glu Asp Ala Thr Ser Ala Gly Glu Leu Gly
            585                 590                 595 ttt act gga att ctt gta tgg atg agg ttc atg gct aca agg caa ctg         2057
Phe Thr Gly Ile Leu Val Trp Met Arg Phe Met Ala Thr Arg Gln Leu
        600                 605                 610 ata tgg aac aaa aac tat aac gta aaa cca cgt gaa ata agc aag gct         2105
Ile Trp Asn Lys Asn Tyr Asn Val Lys Pro Arg Glu Ile Ser Lys Ala
615                 620                 625                 630 cag gac aga ctt aca gac ttg ttg cag aat gct ttc acc agt cac cct         2153
Gln Asp Arg Leu Thr Asp Leu Leu Gln Asn Ala Phe Thr Ser His Pro
                        635                 640                 645 caa tac cgt gaa att ttg cgg atg att atg tca act gtt gga cgt gga         2201
Gln Tyr Arg Glu Ile Leu Arg Met Ile Met Ser Thr Val Gly Arg Gly
                650                 655                 660 ggt gaa ggg gat gta gga cag cga att agg gat gaa att ttg gtc atc         2249
Gly Glu Gly Asp Val Gly Gln Arg Ile Arg Asp Glu Ile Leu Val Ile
            665                 670                 675 cag agg aaa aat gac tgc aag ggt ggt atg atg gaa gaa tgg cat cag         2297
Gln Arg Lys Asn Asp Cys Lys Gly Gly Met Met Glu Glu Trp His Gln
        680                 685                 690 aaa ttg cat aat aat act agt cct gat gat gtt gtg atc tgt cag gca         2345
Lys Leu His Asn Asn Thr Ser Pro Asp Asp Val Val Ile Cys Gln Ala
695                 700                 705                 710 ttg att gac tac atc aag agt gat ttt gat ctt ggt gtt tat tgg aaa         2393
Leu Ile Asp Tyr Ile Lys Ser Asp Phe Asp Leu Gly Val Tyr Trp Lys
                        715                 720                 725 acc ctg aat gag aac gga ata aca aaa gag cgt ctt ttg agt tat gac         2441
Thr Leu Asn Glu Asn Gly Ile Thr Lys Glu Arg Leu Leu Ser Tyr Asp
                730                 735                 740 cgt gct atc cat tct gaa ccg aat ttt aga gga gat caa aag aat ggt         2489
Arg Ala Ile His Ser Glu Pro Asn Phe Arg Gly Asp Gln Lys Asn Gly
            745                 750                 755 ctt ttg cgt gat tta ggt cac tat atg aga aca ttg aag gct gtt cat         2537
Leu Leu Arg Asp Leu Gly His Tyr Met Arg Thr Leu Lys Ala Val His
        760                 765                 770 tca ggt gca gat ctt gag tct gct att gca aac tgc atg ggc tac aaa         2585
Ser Gly Ala Asp Leu Glu Ser Ala Ile Ala Asn Cys Met Gly Tyr Lys
775                 780                 785                 790 act gag gga gaa ggc ttt atg gtt gga gtc cag ata aat cct gta tca         2633
Thr Glu Gly Glu Gly Phe Met Val Gly Val Gln Ile Asn Pro Val Ser
                        795                 800                 805
```

-continued

| | |
|---|---|
| ggc ttg cca tct ggc ttt cag ggc ctc ctc cat ttt gtc tta gac cat<br>Gly Leu Pro Ser Gly Phe Gln Gly Leu Leu His Phe Val Leu Asp His<br>810                    815                    820 | 2681 |
| gtg gaa gat aaa aat gtg gaa act ctt ctt gag gga ttg cta gag gct<br>Val Glu Asp Lys Asn Val Glu Thr Leu Leu Glu Gly Leu Leu Glu Ala<br>825                    830                    835 | 2729 |
| cgt gag gag ctt agg ccc ttg ctt ctc aaa cca aac aac cgt cta aag<br>Arg Glu Glu Leu Arg Pro Leu Leu Leu Lys Pro Asn Asn Arg Leu Lys<br>840                    845                    850 | 2777 |
| gat ctg ctg ttt ttg gac ata gca ctt gat tct aca gtt aga aca gca<br>Asp Leu Leu Phe Leu Asp Ile Ala Leu Asp Ser Thr Val Arg Thr Ala<br>855                    860                    865                    870 | 2825 |
| gta gaa agg gga tat gaa gaa ttg aac aac gct aat cct gag aaa atc<br>Val Glu Arg Gly Tyr Glu Glu Leu Asn Asn Ala Asn Pro Glu Lys Ile<br>                    875                    880                    885 | 2873 |
| atg tac ttc atc tcc ctc gtt ctt gaa aat ctc gca ctc tct gtg gac<br>Met Tyr Phe Ile Ser Leu Val Leu Glu Asn Leu Ala Leu Ser Val Asp<br>                    890                    895                    900 | 2921 |
| gat aat gaa gat ctt gtt tat tgc ttg aag gga tgg aat caa gct ctt<br>Asp Asn Glu Asp Leu Val Tyr Cys Leu Lys Gly Trp Asn Gln Ala Leu<br>905                    910                    915 | 2969 |
| tca atg tcc aat ggt gga gac aac cat tgg gct tta ttt gca aaa gct<br>Ser Met Ser Asn Gly Gly Asp Asn His Trp Ala Leu Phe Ala Lys Ala<br>920                    925                    930 | 3017 |
| gta ctt gac aga atc cgt ctt gca ctt gca agc aag gca gag tgg tac<br>Val Leu Asp Arg Ile Arg Leu Ala Leu Ala Ser Lys Ala Glu Trp Tyr<br>935                    940                    945                    950 | 3065 |
| cat cac tta ttg cag cca tct gcc gaa tat cta gga tca atc ctt ggg<br>His His Leu Leu Gln Pro Ser Ala Glu Tyr Leu Gly Ser Ile Leu Gly<br>                    955                    960                    965 | 3113 |
| gtg gac caa tgg gct ttg aac ata ttt act gaa gaa att ata cgt gct<br>Val Asp Gln Trp Ala Leu Asn Ile Phe Thr Glu Glu Ile Ile Arg Ala<br>970                    975                    980 | 3161 |
| gga tca gca gct tca tta tcc tct ctt ctt aat aga ctc gat ccc gtg<br>Gly Ser Ala Ala Ser Leu Ser Ser Leu Leu Asn Arg Leu Asp Pro Val<br>985                    990                    995 | 3209 |
| ctt cgg aaa act gca aat cta gga agt tgg cag att atc agt cca<br>Leu Arg Lys Thr Ala Asn Leu Gly Ser Trp Gln Ile Ile Ser Pro<br>1000                  1005                  1010 | 3254 |
| gtt gaa gcc gtt gga tat gtt gtc gtt gtg gat gag ttg ctt tca<br>Val Glu Ala Val Gly Tyr Val Val Val Val Asp Glu Leu Leu Ser<br>1015                  1020                  1025 | 3299 |
| gtt cag aat gaa atc tac aag aag ccc acg atc tta gta gca aac<br>Val Gln Asn Glu Ile Tyr Lys Lys Pro Thr Ile Leu Val Ala Asn<br>1030                  1035                  1040 | 3344 |
| tct gtt aaa gga gag gag gaa att cct gat ggt gct gtt gcc ctg<br>Ser Val Lys Gly Glu Glu Glu Ile Pro Asp Gly Ala Val Ala Leu<br>1045                  1050                  1055 | 3389 |
| ata aca cca gac atg cca gat gtt ctt tca cat gtt tct gtt cga<br>Ile Thr Pro Asp Met Pro Asp Val Leu Ser His Val Ser Val Arg<br>1060                  1065                  1070 | 3434 |
| gct aga aat ggg aag gtt tgc ttt gct aca tgc ttt gat ccc aat<br>Ala Arg Asn Gly Lys Val Cys Phe Ala Thr Cys Phe Asp Pro Asn<br>1075                  1080                  1085 | 3479 |
| ata ttg gct gac ctc caa gca aag gaa gga agg att ttg ctc tta<br>Ile Leu Ala Asp Leu Gln Ala Lys Glu Gly Arg Ile Leu Leu Leu<br>1090                  1095                  1100 | 3524 |
| aag cct aca cct tca gac ata atc tat agt gag gtg aat gag att<br>Lys Pro Thr Pro Ser Asp Ile Ile Tyr Ser Glu Val Asn Glu Ile<br>1105                  1110                  1115 | 3569 |

-continued

| | | |
|---|---|---|
| gag ctc caa agt tca agt aac ttg gta gaa gct gaa act tca gca<br>Glu Leu Gln Ser Ser Ser Asn Leu Val Glu Ala Glu Thr Ser Ala<br>1120               1125                  1130 | 3614 |
| aca ctt aga ttg gtg aaa aag caa ttt ggt ggt tgt tac gca ata<br>Thr Leu Arg Leu Val Lys Lys Gln Phe Gly Gly Cys Tyr Ala Ile<br>1135               1140                  1145 | 3659 |
| tca gca gat gaa ttc aca agt gaa atg gtt gga gct aaa tca cgt<br>Ser Ala Asp Glu Phe Thr Ser Glu Met Val Gly Ala Lys Ser Arg<br>1150               1155                  1160 | 3704 |
| aat att gca tat ctg aaa gga aaa gtg cct tcc tcg gtg gga att<br>Asn Ile Ala Tyr Leu Lys Gly Lys Val Pro Ser Ser Val Gly Ile<br>1165               1170                  1175 | 3749 |
| cct acg tca gta gct ctt cca ttt gga gtc ttt gag aaa gta ctt<br>Pro Thr Ser Val Ala Leu Pro Phe Gly Val Phe Glu Lys Val Leu<br>1180               1185                  1190 | 3794 |
| tca gac gac ata aat cag gga gtg gca aaa gag ttg caa att ctg<br>Ser Asp Asp Ile Asn Gln Gly Val Ala Lys Glu Leu Gln Ile Leu<br>1195               1200                  1205 | 3839 |
| acg aaa aaa cta tct gaa gga gac ttc agc gct ctt ggt gaa att<br>Thr Lys Lys Leu Ser Glu Gly Asp Phe Ser Ala Leu Gly Glu Ile<br>1210               1215                  1220 | 3884 |
| cgc aca acg att tta gat ctt tca gca cca gct caa ttg gtc aaa<br>Arg Thr Thr Ile Leu Asp Leu Ser Ala Pro Ala Gln Leu Val Lys<br>1225               1230                  1235 | 3929 |
| gag ctg aag gaa aag atg cag ggt tct ggc atg cct tgg cct ggt<br>Glu Leu Lys Glu Lys Met Gln Gly Ser Gly Met Pro Trp Pro Gly<br>1240               1245                  1250 | 3974 |
| gat gaa ggt cca aag cgg tgg gaa caa gca tgg atg gcc ata aaa<br>Asp Glu Gly Pro Lys Arg Trp Glu Gln Ala Trp Met Ala Ile Lys<br>1255               1260                  1265 | 4019 |
| aag gtg tgg gct tca aaa tgg aat gag aga gca tac ttc agc aca<br>Lys Val Trp Ala Ser Lys Trp Asn Glu Arg Ala Tyr Phe Ser Thr<br>1270               1275                  1280 | 4064 |
| agg aag gtg aaa ctg gat cat gac tat ctg tgc atg gct gtc ctt<br>Arg Lys Val Lys Leu Asp His Asp Tyr Leu Cys Met Ala Val Leu<br>1285               1290                  1295 | 4109 |
| gtt caa gaa ata ata aat gct gat tat gca ttt gtc att cac aca<br>Val Gln Glu Ile Ile Asn Ala Asp Tyr Ala Phe Val Ile His Thr<br>1300               1305                  1310 | 4154 |
| acc aac cca tct tcc gga gac gac tca gaa ata tat gcc gag gtg<br>Thr Asn Pro Ser Ser Gly Asp Asp Ser Glu Ile Tyr Ala Glu Val<br>1315               1320                  1325 | 4199 |
| gtc agg ggc ctt ggg gaa aca ctt gtt gga gct tac cca gga cgt<br>Val Arg Gly Leu Gly Glu Thr Leu Val Gly Ala Tyr Pro Gly Arg<br>1330               1335                  1340 | 4244 |
| gct ttg agt ttt atc tgc aag aaa aag gat ctc aac tct cct caa<br>Ala Leu Ser Phe Ile Cys Lys Lys Lys Asp Leu Asn Ser Pro Gln<br>1345               1350                  1355 | 4289 |
| gtg tta ggt tac cca agc aaa ccg atc ggc ctt ttc ata aaa aga<br>Val Leu Gly Tyr Pro Ser Lys Pro Ile Gly Leu Phe Ile Lys Arg<br>1360               1365                  1370 | 4334 |
| tct atc atc ttc cga tct gat tcc aat ggg gaa gat ttg gaa ggt<br>Ser Ile Ile Phe Arg Ser Asp Ser Asn Gly Glu Asp Leu Glu Gly<br>1375               1380                  1385 | 4379 |
| tat gcc ggt gct ggc ctc tac gac agt gta cca atg gat gag gag<br>Tyr Ala Gly Ala Gly Leu Tyr Asp Ser Val Pro Met Asp Glu Glu<br>1390               1395                  1400 | 4424 |
| gaa aaa gtt gta att gat tac tct tcc gac cca ttg ata act gat<br>Glu Lys Val Val Ile Asp Tyr Ser Ser Asp Pro Leu Ile Thr Asp | 4469 |

```
                1405                1410                1415
ggt aac ttc cgc cag aca atc ctg tcc aac att gct cgt gct gga      4514
Gly Asn Phe Arg Gln Thr Ile Leu Ser Asn Ile Ala Arg Ala Gly
    1420                1425                1430 cat gct atc gag gag cta tat ggc tct cct caa gac atc gag ggt      4559
His Ala Ile Glu Glu Leu Tyr Gly Ser Pro Gln Asp Ile Glu Gly
1435                1440                1445 gta gtg agg gat gga aag att tat gtc gtt cag aca aga cct cag      4604
Val Val Arg Asp Gly Lys Ile Tyr Val Val Gln Thr Arg Pro Gln
    1450                1455                1460 atg tgatcatatt ctcgttgtat gttgttcaga aagaccata gatgtgatca        4657
Met tattctcatg gtatcagatc tgtgaccact tacctcccat gaagttgcct gtatgattat  4717
acgtgatcca aagccatcac atcatgttca ccttcagcta ttggaggaga agtgagaagt  4777
aggaattgca atatgaggaa taataagaaa aactttgtag aagttaaatt agctgggtat  4837
gatataggga gaaatgtgta acattgtac tatatatagt atacacacgc attatgtatt   4897
tgcattatgc actgaataat atcgcagcat caaagaagaa atcctttgag tggtttcaat  4957
tgccgcggcc gcgaattcct gcagcccggg ggatccacta gttctagagc ggccgccacc  5017
gcggtggagc tccagctttt gttcccttta gtgagggtta attt                  5061
```

<210> SEQ ID NO 6
<211> LENGTH: 1464
<212> TYPE: PRT
<213> ORGANISM: Solanum tuberosum

<400> SEQUENCE: 6

Met Ser Asn Ser Leu Gly Asn Asn Leu Leu Tyr Gln Gly Phe Leu Thr
1               5                   10                  15

Ser Thr Val Leu Glu His Lys Ser Arg Ile Ser Pro Pro Cys Val Gly
            20                  25                  30

Gly Asn Ser Leu Phe Gln Gln Gln Val Ile Ser Lys Ser Pro Leu Ser
        35                  40                  45

Thr Glu Phe Arg Gly Asn Arg Leu Lys Val Gln Lys Lys Ile Pro
    50                  55                  60

Met Gly Lys Asn Arg Ala Phe Ser Ser Pro His Ala Val Leu Thr
65                  70                  75                  80

Thr Asp Thr Ser Ser Glu Leu Ala Glu Lys Phe Ser Leu Glu Gly Asn
                85                  90                  95

Ile Glu Leu Gln Val Asp Val Arg Pro Pro Thr Ser Gly Asp Val Ser
            100                 105                 110

Phe Val Asp Phe Gln Ala Thr Asn Gly Ser Asp Lys Leu Phe Leu His
        115                 120                 125

Trp Gly Ala Val Lys Phe Gly Lys Glu Thr Trp Ser Leu Pro Asn Asp
    130                 135                 140

Arg Pro Asp Gly Thr Lys Val Tyr Lys Asn Lys Ala Leu Arg Thr Pro
145                 150                 155                 160

Phe Val Lys Ser Gly Ser Asn Ser Ile Leu Arg Leu Glu Ile Arg Asp
                165                 170                 175

Thr Ala Ile Glu Ala Ile Glu Phe Leu Ile Tyr Asp Glu Ala Tyr Asp
            180                 185                 190

Lys Trp Ile Lys Asn Asn Gly Gly Asn Phe Arg Val Lys Leu Ser Arg
        195                 200                 205

Lys Glu Ile Arg Gly Pro Asp Val Ser Val Pro Glu Glu Leu Val Gln

-continued

```
            210                 215                 220
Ile Gln Ser Tyr Leu Arg Trp Glu Arg Lys Gly Lys Gln Asn Tyr Thr
225                 230                                     240

Pro Glu Lys Glu Lys Glu Glu Tyr Glu Ala Ala Arg Thr Glu Leu Gln
                245                 250                 255

Glu Glu Ile Ala Arg Gly Ala Ser Ile Gln Asp Ile Arg Ala Arg Leu
            260                 265                 270

Thr Lys Thr Asn Asp Lys Ser Gln Ser Lys Glu Glu Pro Leu His Val
        275                 280                 285

Thr Lys Ser Glu Ile Pro Asp Asp Leu Ala Gln Ala Gln Ala Tyr Ile
    290                 295                 300

Arg Trp Glu Lys Ala Gly Lys Pro Asn Tyr Pro Pro Glu Lys Gln Ile
305                 310                 315                 320

Glu Glu Leu Glu Glu Ala Arg Arg Glu Leu Gln Leu Glu Leu Glu Lys
                325                 330                 335

Gly Ile Thr Leu Asp Glu Leu Arg Lys Lys Ile Thr Lys Gly Glu Ile
            340                 345                 350

Lys Thr Lys Ala Glu Lys His Val Lys Arg Ser Ser Phe Ala Val Glu
        355                 360                 365

Arg Ile Gln Arg Lys Arg Asp Phe Gly Gln Leu Ile Asn Lys Tyr
    370                 375                 380

Pro Ser Ser Pro Ala Val Gln Val Gln Lys Val Leu Glu Glu Pro Pro
385                 390                 395                 400

Ala Leu Ser Lys Ile Lys Leu Tyr Ala Lys Glu Lys Glu Glu Gln Ile
                405                 410                 415

Asp Asp Pro Ile Leu Asn Lys Lys Ile Phe Lys Val Asp Asp Gly Glu
            420                 425                 430

Leu Leu Val Leu Val Ala Lys Ser Gly Lys Thr Lys Val His Ile
        435                 440                 445

Ala Thr Asp Leu Asn Gln Pro Ile Thr Leu His Trp Ala Leu Ser Lys
    450                 455                 460

Ser Arg Gly Glu Trp Met Val Pro Pro Ser Ser Ile Leu Pro Pro Gly
465                 470                 475                 480

Ser Ile Ile Leu Asp Lys Ala Ala Glu Thr Pro Phe Ser Ala Ser Ser
                485                 490                 495

Ser Asp Gly Leu Thr Ser Lys Val Gln Ser Leu Asp Ile Val Ile Glu
            500                 505                 510

Asp Gly Asn Phe Val Gly Met Pro Phe Val Leu Leu Ser Gly Glu Lys
        515                 520                 525

Trp Ile Lys Asn Gln Gly Ser Asp Phe Tyr Val Asp Phe Ser Ala Ala
    530                 535                 540

Ser Lys Leu Ala Leu Lys Ala Gly Asp Gly Ser Gly Thr Ala Lys
545                 550                 555                 560

Ser Leu Leu Asp Lys Ile Ala Asp Met Glu Ser Glu Ala Gln Lys Ser
                565                 570                 575

Phe Met His Arg Phe Asn Ile Ala Ala Asp Leu Ile Glu Asp Ala Thr
            580                 585                 590

Ser Ala Gly Glu Leu Gly Phe Thr Gly Ile Leu Val Trp Met Arg Phe
        595                 600                 605

Met Ala Thr Arg Gln Leu Ile Trp Asn Lys Asn Tyr Asn Val Lys Pro
    610                 615                 620

Arg Glu Ile Ser Lys Ala Gln Asp Arg Leu Thr Asp Leu Leu Gln Asn
625                 630                 635                 640
```

-continued

```
Ala Phe Thr Ser His Pro Gln Tyr Arg Glu Ile Leu Arg Met Ile Met
            645                 650                 655

Ser Thr Val Gly Arg Gly Gly Glu Gly Asp Val Gly Gln Arg Ile Arg
        660                 665                 670

Asp Glu Ile Leu Val Ile Gln Arg Lys Asn Asp Cys Lys Gly Gly Met
            675                 680             685

Met Glu Glu Trp His Gln Lys Leu His Asn Asn Thr Ser Pro Asp Asp
    690                 695                 700

Val Val Ile Cys Gln Ala Leu Ile Asp Tyr Ile Lys Ser Asp Phe Asp
705                 710                 715                 720

Leu Gly Val Tyr Trp Lys Thr Leu Asn Glu Asn Gly Ile Thr Lys Glu
                725                 730                 735

Arg Leu Leu Ser Tyr Asp Arg Ala Ile His Ser Glu Pro Asn Phe Arg
                740                 745                 750

Gly Asp Gln Lys Asn Gly Leu Leu Arg Asp Leu Gly His Tyr Met Arg
            755                 760                 765

Thr Leu Lys Ala Val His Ser Gly Ala Asp Leu Glu Ser Ala Ile Ala
770                 775                 780

Asn Cys Met Gly Tyr Lys Thr Glu Gly Glu Gly Phe Met Val Gly Val
785                 790                 795                 800

Gln Ile Asn Pro Val Ser Gly Leu Pro Ser Gly Phe Gln Gly Leu Leu
                805                 810                 815

His Phe Val Leu Asp His Val Glu Asp Lys Asn Val Glu Thr Leu Leu
                820                 825                 830

Glu Gly Leu Leu Glu Ala Arg Glu Glu Leu Arg Pro Leu Leu Leu Lys
            835                 840                 845

Pro Asn Asn Arg Leu Lys Asp Leu Leu Phe Leu Asp Ile Ala Leu Asp
            850                 855                 860

Ser Thr Val Arg Thr Ala Val Glu Arg Gly Tyr Glu Glu Leu Asn Asn
865                 870                 875                 880

Ala Asn Pro Glu Lys Ile Met Tyr Phe Ile Ser Leu Val Leu Glu Asn
                885                 890                 895

Leu Ala Leu Ser Val Asp Asp Asn Glu Asp Leu Val Tyr Cys Leu Lys
                900                 905                 910

Gly Trp Asn Gln Ala Leu Ser Met Ser Asn Gly Gly Asp Asn His Trp
            915                 920                 925

Ala Leu Phe Ala Lys Ala Val Leu Asp Arg Ile Arg Leu Ala Leu Ala
            930                 935                 940

Ser Lys Ala Glu Trp Tyr His His Leu Leu Gln Pro Ser Ala Glu Tyr
945                 950                 955                 960

Leu Gly Ser Ile Leu Gly Val Asp Gln Trp Ala Leu Asn Ile Phe Thr
                965                 970                 975

Glu Glu Ile Ile Arg Ala Gly Ser Ala Ala Ser Leu Ser Leu Leu
            980                 985                 990

Asn Arg Leu Asp Pro Val Leu Arg Lys Thr Ala Asn Leu Gly Ser Trp
        995                 1000                1005

Gln Ile Ile Ser Pro Val Glu Ala Val Gly Tyr Val Val Val Val
    1010                1015                1020

Asp Glu Leu Leu Ser Val Gln Asn Glu Ile Tyr Lys Lys Pro Thr
    1025                1030                1035

Ile Leu Val Ala Asn Ser Val Lys Gly Glu Glu Glu Ile Pro Asp
    1040                1045                1050
```

-continued

| | | | | | | | | | | |
|---|---|---|---|---|---|---|---|---|---|---|
| Gly | Ala | Val | Ala | Leu | Ile | Thr | Pro | Asp | Met | Pro | Asp | Val | Leu | Ser |
| | 1055 | | | | 1060 | | | | 1065 | |
| His | Val | Ser | Val | Arg | Ala | Arg | Asn | Gly | Lys | Val | Cys | Phe | Ala | Thr |
| | 1070 | | | | 1075 | | | | 1080 | |
| Cys | Phe | Asp | Pro | Asn | Ile | Leu | Ala | Asp | Leu | Gln | Ala | Lys | Glu | Gly |
| | 1085 | | | | 1090 | | | | 1095 | |
| Arg | Ile | Leu | Leu | Leu | Lys | Pro | Thr | Pro | Ser | Asp | Ile | Ile | Tyr | Ser |
| | 1100 | | | | 1105 | | | | 1110 | |
| Glu | Val | Asn | Glu | Ile | Glu | Leu | Gln | Ser | Ser | Asn | Leu | Val | Glu |
| | 1115 | | | | 1120 | | | | 1125 | |
| Ala | Glu | Thr | Ser | Ala | Thr | Leu | Arg | Leu | Val | Lys | Lys | Gln | Phe | Gly |
| | 1130 | | | | 1135 | | | | 1140 | |
| Gly | Cys | Tyr | Ala | Ile | Ser | Ala | Asp | Glu | Phe | Thr | Ser | Glu | Met | Val |
| | 1145 | | | | 1150 | | | | 1155 | |
| Gly | Ala | Lys | Ser | Arg | Asn | Ile | Ala | Tyr | Leu | Lys | Gly | Lys | Val | Pro |
| | 1160 | | | | 1165 | | | | 1170 | |
| Ser | Ser | Val | Gly | Ile | Pro | Thr | Ser | Val | Ala | Leu | Pro | Phe | Gly | Val |
| | 1175 | | | | 1180 | | | | 1185 | |
| Phe | Glu | Lys | Val | Leu | Ser | Asp | Asp | Ile | Asn | Gln | Gly | Val | Ala | Lys |
| | 1190 | | | | 1195 | | | | 1200 | |
| Glu | Leu | Gln | Ile | Leu | Thr | Lys | Lys | Leu | Ser | Glu | Gly | Asp | Phe | Ser |
| | 1205 | | | | 1210 | | | | 1215 | |
| Ala | Leu | Gly | Glu | Ile | Arg | Thr | Thr | Ile | Leu | Asp | Leu | Ser | Ala | Pro |
| | 1220 | | | | 1225 | | | | 1230 | |
| Ala | Gln | Leu | Val | Lys | Glu | Leu | Lys | Glu | Lys | Met | Gln | Gly | Ser | Gly |
| | 1235 | | | | 1240 | | | | 1245 | |
| Met | Pro | Trp | Pro | Gly | Asp | Glu | Gly | Pro | Lys | Arg | Trp | Glu | Gln | Ala |
| | 1250 | | | | 1255 | | | | 1260 | |
| Trp | Met | Ala | Ile | Lys | Lys | Val | Trp | Ala | Ser | Lys | Trp | Asn | Glu | Arg |
| | 1265 | | | | 1270 | | | | 1275 | |
| Ala | Tyr | Phe | Ser | Thr | Arg | Lys | Val | Lys | Leu | Asp | His | Asp | Tyr | Leu |
| | 1280 | | | | 1285 | | | | 1290 | |
| Cys | Met | Ala | Val | Leu | Val | Gln | Glu | Ile | Ile | Asn | Ala | Asp | Tyr | Ala |
| | 1295 | | | | 1300 | | | | 1305 | |
| Phe | Val | Ile | His | Thr | Thr | Asn | Pro | Ser | Ser | Gly | Asp | Asp | Ser | Glu |
| | 1310 | | | | 1315 | | | | 1320 | |
| Ile | Tyr | Ala | Glu | Val | Val | Arg | Gly | Leu | Gly | Glu | Thr | Leu | Val | Gly |
| | 1325 | | | | 1330 | | | | 1335 | |
| Ala | Tyr | Pro | Gly | Arg | Ala | Leu | Ser | Phe | Ile | Cys | Lys | Lys | Lys | Asp |
| | 1340 | | | | 1345 | | | | 1350 | |
| Leu | Asn | Ser | Pro | Gln | Val | Leu | Gly | Tyr | Pro | Ser | Lys | Pro | Ile | Gly |
| | 1355 | | | | 1360 | | | | 1365 | |
| Leu | Phe | Ile | Lys | Arg | Ser | Ile | Ile | Phe | Arg | Ser | Asp | Ser | Asn | Gly |
| | 1370 | | | | 1375 | | | | 1380 | |
| Glu | Asp | Leu | Glu | Gly | Tyr | Ala | Gly | Ala | Gly | Leu | Tyr | Asp | Ser | Val |
| | 1385 | | | | 1390 | | | | 1395 | |
| Pro | Met | Asp | Glu | Glu | Glu | Lys | Val | Val | Ile | Asp | Tyr | Ser | Ser | Asp |
| | 1400 | | | | 1405 | | | | 1410 | |
| Pro | Leu | Ile | Thr | Asp | Gly | Asn | Phe | Arg | Gln | Thr | Ile | Leu | Ser | Asn |
| | 1415 | | | | 1420 | | | | 1425 | |
| Ile | Ala | Arg | Ala | Gly | His | Ala | Ile | Glu | Glu | Leu | Tyr | Gly | Ser | Pro |
| | 1430 | | | | 1435 | | | | 1440 | |
| Gln | Asp | Ile | Glu | Gly | Val | Val | Arg | Asp | Gly | Lys | Ile | Tyr | Val | Val |

-continued

```
                    1445                1450                1455
          Gln Thr  Arg Pro Gln Met
               1460

<210> SEQ ID NO 7
<211> LENGTH: 1641
<212> TYPE: DNA
<213> ORGANISM: Solanum tuberosum
<220> FEATURE:
<221> NAME/KEY: CDS
<222> LOCATION: (1)..(1638)
<223> OTHER INFORMATION:

<400> SEQUENCE: 7 atg aag cac agt tca gct att tcc gct gtt ttg acc gat gac aat tcg    48
Met Lys His Ser Ser Ala Ile Ser Ala Val Leu Thr Asp Asp Asn Ser
1               5                   10                  15 aca atg gca ccc cta gag gaa gat gtc aag act gaa aat att ggc ctc    96
Thr Met Ala Pro Leu Glu Glu Asp Val Lys Thr Glu Asn Ile Gly Leu
            20                  25                  30 cta aat ttg gat cca act ttg gaa cct tat cta gat cac ttc aga cac   144
Leu Asn Leu Asp Pro Thr Leu Glu Pro Tyr Leu Asp His Phe Arg His
        35                  40                  45 aga atg aag aga tat gtg gat cag aaa atg ctc att gaa aaa tat gag   192
Arg Met Lys Arg Tyr Val Asp Gln Lys Met Leu Ile Glu Lys Tyr Glu
    50                  55                  60 gga ccc ctt gag gaa ttt gct caa ggt tat tta aaa ttt gga ttc aac   240
Gly Pro Leu Glu Glu Phe Ala Gln Gly Tyr Leu Lys Phe Gly Phe Asn
65                  70                  75                  80 agg gaa gat ggt tgc ata gtc tat cgt gaa tgg gct cct gct gct cag   288
Arg Glu Asp Gly Cys Ile Val Tyr Arg Glu Trp Ala Pro Ala Ala Gln
                85                  90                  95 gaa gca gaa gtt att ggc gat ttc aat gga tgg aac ggt tct aac cac   336
Glu Ala Glu Val Ile Gly Asp Phe Asn Gly Trp Asn Gly Ser Asn His
            100                 105                 110 atg atg gag aag gac cag ttt ggt gtt tgg agt att aga att cct gat   384
Met Met Glu Lys Asp Gln Phe Gly Val Trp Ser Ile Arg Ile Pro Asp
        115                 120                 125 gtt gac agt aag cca gtc att cca cac aac tcc aga gtt aag ttt cgt   432
Val Asp Ser Lys Pro Val Ile Pro His Asn Ser Arg Val Lys Phe Arg
    130                 135                 140 ttc aaa cat ggt aat gga gtg tgg gta gat cgt atc cct gct tgg ata   480
Phe Lys His Gly Asn Gly Val Trp Val Asp Arg Ile Pro Ala Trp Ile
145                 150                 155                 160 aag tat gcc act gca gac gcc aca aag ttt gca gca cca tat gat ggt   528
Lys Tyr Ala Thr Ala Asp Ala Thr Lys Phe Ala Ala Pro Tyr Asp Gly
                165                 170                 175 gtc tac tgg gac cca cca cct tca gaa agg tac cac ttc aaa tac cct   576
Val Tyr Trp Asp Pro Pro Pro Ser Glu Arg Tyr His Phe Lys Tyr Pro
            180                 185                 190 cgc cct ccc aaa ccc cga gcc cca cga atc tac gaa gca cat gtc ggc   624
Arg Pro Pro Lys Pro Arg Ala Pro Arg Ile Tyr Glu Ala His Val Gly
        195                 200                 205 atg agc agc tct gag cca cgt gta aat tcg tat cgt gag ttt gca gat   672
Met Ser Ser Ser Glu Pro Arg Val Asn Ser Tyr Arg Glu Phe Ala Asp
    210                 215                 220 gat gtt tta cct cgg att aag gca aat aac tat aat act gtc cag ttg   720
Asp Val Leu Pro Arg Ile Lys Ala Asn Asn Tyr Asn Thr Val Gln Leu
225                 230                 235                 240 atg gcc ata atg gaa cat tct tac tat gga tca ttt gga tat cat gtt   768
Met Ala Ile Met Glu His Ser Tyr Tyr Gly Ser Phe Gly Tyr His Val
```

-continued

```
                    245                 250                 255
aca aac ttt ttt gct gtg agc aat aga tat gga aac ccg gag gac cta       816
Thr Asn Phe Phe Ala Val Ser Asn Arg Tyr Gly Asn Pro Glu Asp Leu
            260                 265                 270 aag tat ctg ata gat aaa gca cat agc ttg ggt tta cag gtt ctg gtg       864
Lys Tyr Leu Ile Asp Lys Ala His Ser Leu Gly Leu Gln Val Leu Val
            275                 280                 285 gat gta gtt cac agt cat gca agc aat aat gtc act gat ggc ctc aat       912
Asp Val Val His Ser His Ala Ser Asn Asn Val Thr Asp Gly Leu Asn
290                 295                 300 ggc ttt gat att ggc caa ggt tct caa gaa tcc tac ttt cat gct gga       960
Gly Phe Asp Ile Gly Gln Gly Ser Gln Glu Ser Tyr Phe His Ala Gly
305                 310                 315                 320 gag cga ggg tac cat aag ttg tgg gat agc agg ctg ttc aac tat gcc      1008
Glu Arg Gly Tyr His Lys Leu Trp Asp Ser Arg Leu Phe Asn Tyr Ala
                325                 330                 335 aat tgg gag gtt ctt cgt ttc ctt ctt tcc aac ttg agg tgg tgg cta      1056
Asn Trp Glu Val Leu Arg Phe Leu Leu Ser Asn Leu Arg Trp Trp Leu
            340                 345                 350 gaa gag tat aac ttt gac gga ttt cga ttt gat gga ata act tct atg      1104
Glu Glu Tyr Asn Phe Asp Gly Phe Arg Phe Asp Gly Ile Thr Ser Met
            355                 360                 365 ctg tat gtt cat cat gga atc aat atg gga ttt aca gga aac tat aat      1152
Leu Tyr Val His His Gly Ile Asn Met Gly Phe Thr Gly Asn Tyr Asn
370                 375                 380 gag tat ttc agc gag gct aca gat gtt gat gct gtg gtc tat tta atg      1200
Glu Tyr Phe Ser Glu Ala Thr Asp Val Asp Ala Val Val Tyr Leu Met
385                 390                 395                 400 ttg gcc aat aat ctg att cac aag att ttc cca gac gca act gtt att      1248
Leu Ala Asn Asn Leu Ile His Lys Ile Phe Pro Asp Ala Thr Val Ile
                405                 410                 415 gcc gaa gat gtt tct ggt atg ccg ggc ctt agc cgg cct gtt tct gag      1296
Ala Glu Asp Val Ser Gly Met Pro Gly Leu Ser Arg Pro Val Ser Glu
            420                 425                 430 gga gga att ggt ttt gat tac cgc ctg gca atg gca atc cca gat aag      1344
Gly Gly Ile Gly Phe Asp Tyr Arg Leu Ala Met Ala Ile Pro Asp Lys
            435                 440                 445 tgg ata gat tat tta aag aat aag aat gat gaa gat tgg tcc atg aag      1392
Trp Ile Asp Tyr Leu Lys Asn Lys Asn Asp Glu Asp Trp Ser Met Lys
450                 455                 460 gaa gta aca tcg agt ttg aca aat agg aga tat aca gag aag tgt ata      1440
Glu Val Thr Ser Ser Leu Thr Asn Arg Arg Tyr Thr Glu Lys Cys Ile
465                 470                 475                 480 gca tat gcg gag agc cat gat cag tct att gtc ggt gac aag acc att      1488
Ala Tyr Ala Glu Ser His Asp Gln Ser Ile Val Gly Asp Lys Thr Ile
                485                 490                 495 gca ttt ctc cta atg gac aaa gag atg tat tct ggc atg tct tgc ttg      1536
Ala Phe Leu Leu Met Asp Lys Glu Met Tyr Ser Gly Met Ser Cys Leu
            500                 505                 510 aca gat gct tct cct gtt gtt gat cga gga att gcg ctt cac aag atg      1584
Thr Asp Ala Ser Pro Val Val Asp Arg Gly Ile Ala Leu His Lys Met
            515                 520                 525 atc cat ttt ttt cac aat ggc ctt ggg agg aga ggg gta cct caa ttt      1632
Ile His Phe Phe His Asn Gly Leu Gly Arg Arg Gly Val Pro Gln Phe
530                 535                 540 cat ggg taa                                                          1641
His Gly
545
```

<210> SEQ ID NO 8
<211> LENGTH: 546
<212> TYPE: PRT
<213> ORGANISM: Solanum tuberosum

<400> SEQUENCE: 8

| Met | Lys | His | Ser | Ser | Ala | Ile | Ser | Ala | Val | Leu | Thr | Asp | Asp | Asn | Ser |
|---|---|---|---|---|---|---|---|---|---|---|---|---|---|---|---|
| 1 | | | | 5 | | | | | 10 | | | | | 15 | |

Thr Met Ala Pro Leu Glu Glu Asp Val Lys Thr Glu Asn Ile Gly Leu
            20                  25                  30

Leu Asn Leu Asp Pro Thr Leu Glu Pro Tyr Leu Asp His Phe Arg His
            35                  40                  45

Arg Met Lys Arg Tyr Val Asp Gln Lys Met Leu Ile Glu Lys Tyr Glu
 50                  55                  60

Gly Pro Leu Glu Glu Phe Ala Gln Gly Tyr Leu Lys Phe Gly Phe Asn
 65                  70                  75                  80

Arg Glu Asp Gly Cys Ile Val Tyr Arg Glu Trp Ala Pro Ala Ala Gln
            85                  90                  95

Glu Ala Glu Val Ile Gly Asp Phe Asn Gly Trp Asn Gly Ser Asn His
            100                 105                 110

Met Met Glu Lys Asp Gln Phe Gly Val Trp Ser Ile Arg Ile Pro Asp
            115                 120                 125

Val Asp Ser Lys Pro Val Ile Pro His Asn Ser Arg Val Lys Phe Arg
130                 135                 140

Phe Lys His Gly Asn Gly Val Trp Val Asp Arg Ile Pro Ala Trp Ile
145                 150                 155                 160

Lys Tyr Ala Thr Ala Asp Ala Thr Lys Phe Ala Ala Pro Tyr Asp Gly
            165                 170                 175

Val Tyr Trp Asp Pro Pro Ser Glu Arg Tyr His Phe Lys Tyr Pro
            180                 185                 190

Arg Pro Pro Lys Pro Arg Ala Pro Arg Ile Tyr Glu Ala His Val Gly
            195                 200                 205

Met Ser Ser Ser Glu Pro Arg Val Asn Ser Tyr Arg Glu Phe Ala Asp
210                 215                 220

Asp Val Leu Pro Arg Ile Lys Ala Asn Asn Tyr Asn Thr Val Gln Leu
225                 230                 235                 240

Met Ala Ile Met Glu His Ser Tyr Tyr Gly Ser Phe Gly Tyr His Val
            245                 250                 255

Thr Asn Phe Phe Ala Val Ser Asn Arg Tyr Gly Asn Pro Glu Asp Leu
            260                 265                 270

Lys Tyr Leu Ile Asp Lys Ala His Ser Leu Gly Leu Gln Val Leu Val
            275                 280                 285

Asp Val Val His Ser His Ala Ser Asn Asn Val Thr Asp Gly Leu Asn
290                 295                 300

Gly Phe Asp Ile Gly Gln Gly Ser Gln Glu Ser Tyr Phe His Ala Gly
305                 310                 315                 320

Glu Arg Gly Tyr His Lys Leu Trp Asp Ser Arg Leu Phe Asn Tyr Ala
            325                 330                 335

Asn Trp Glu Val Leu Arg Phe Leu Leu Ser Asn Leu Arg Trp Trp Leu
            340                 345                 350

Glu Glu Tyr Asn Phe Asp Gly Phe Arg Phe Asp Gly Ile Thr Ser Met
            355                 360                 365

Leu Tyr Val His His Gly Ile Asn Met Gly Phe Thr Gly Asn Tyr Asn
370                 375                 380

```
Glu Tyr Phe Ser Glu Ala Thr Asp Val Asp Ala Val Val Tyr Leu Met
385                 390                 395                 400

Leu Ala Asn Asn Leu Ile His Lys Ile Phe Pro Asp Ala Thr Val Ile
            405                 410                 415

Ala Glu Asp Val Ser Gly Met Pro Gly Leu Ser Arg Pro Val Ser Glu
        420                 425                 430

Gly Gly Ile Gly Phe Asp Tyr Arg Leu Ala Met Ala Ile Pro Asp Lys
        435                 440                 445

Trp Ile Asp Tyr Leu Lys Asn Lys Asn Asp Glu Asp Trp Ser Met Lys
450                 455                 460

Glu Val Thr Ser Ser Leu Thr Asn Arg Arg Tyr Thr Glu Lys Cys Ile
465                 470                 475                 480

Ala Tyr Ala Glu Ser His Asp Gln Ser Ile Val Gly Asp Lys Thr Ile
            485                 490                 495

Ala Phe Leu Leu Met Asp Lys Glu Met Tyr Ser Gly Met Ser Cys Leu
        500                 505                 510

Thr Asp Ala Ser Pro Val Val Asp Arg Gly Ile Ala Leu His Lys Met
        515                 520                 525

Ile His Phe Phe His Asn Gly Leu Gly Arg Arg Gly Val Pro Gln Phe
530                 535                 540

His Gly
545

<210> SEQ ID NO 9
<211> LENGTH: 822
<212> TYPE: PRT
<213> ORGANISM: Zea mays

<400> SEQUENCE: 9

Leu Cys Leu Val Ser Pro Ser Ser Pro Thr Pro Leu Pro Pro Pro
1               5                   10                  15

Arg Arg Ser Arg Ser His Ala Asp Arg Ala Ala Pro Pro Gly Ile Ala
            20                  25                  30

Gly Gly Gly Asn Val Arg Leu Ser Val Leu Ser Val Gln Cys Lys Ala
        35                  40                  45

Arg Arg Ser Gly Val Arg Lys Val Lys Ser Lys Phe Ala Thr Ala Ala
    50                  55                  60

Thr Val Gln Glu Asp Lys Thr Met Ala Thr Ala Lys Gly Asp Val Asp
65                  70                  75                  80

His Leu Pro Ile Tyr Asp Leu Asp Pro Lys Leu Glu Ile Phe Lys Asp
                85                  90                  95

His Phe Arg Tyr Arg Met Lys Arg Phe Leu Glu Gln Lys Gly Ser Ile
            100                 105                 110

Glu Glu Asn Glu Gly Ser Leu Glu Ser Phe Ser Lys Gly Tyr Leu Lys
        115                 120                 125

Phe Gly Ile Asn Thr Asn Glu Asp Gly Thr Val Tyr Arg Glu Trp Ala
    130                 135                 140

Pro Ala Ala Gln Glu Ala Glu Leu Ile Gly Asp Phe Asn Asp Trp Asn
145                 150                 155                 160

Gly Ala Asn His Lys Met Glu Lys Asp Lys Phe Gly Val Trp Ser Ile
                165                 170                 175

Lys Ile Asp His Val Lys Gly Lys Pro Ala Ile Pro His Asn Ser Lys
            180                 185                 190

Val Lys Phe Arg Phe Leu His Gly Gly Val Trp Val Asp Arg Ile Pro
        195                 200                 205
```

```
Ala Leu Ile Arg Tyr Ala Thr Val Asp Ala Ser Lys Phe Gly Ala Pro
            210                 215                 220

Tyr Asp Gly Val His Trp Asp Pro Ala Ser Glu Arg Tyr Thr Phe
225                 230                 235                 240

Lys His Pro Arg Pro Ser Lys Pro Ala Ala Pro Arg Ile Tyr Glu Ala
                245                 250                 255

His Val Gly Met Ser Gly Glu Lys Pro Ala Val Ser Thr Tyr Arg Glu
            260                 265                 270

Phe Ala Asp Asn Val Leu Pro Arg Ile Arg Ala Asn Asn Tyr Asn Thr
            275                 280                 285

Val Gln Leu Met Ala Val Met Glu His Ser Tyr Tyr Ala Ser Phe Gly
            290                 295                 300

Tyr His Val Thr Asn Phe Phe Ala Val Ser Ser Arg Ser Gly Thr Pro
305                 310                 315                 320

Glu Asp Leu Lys Tyr Leu Val Asp Lys Ala His Ser Leu Gly Leu Arg
                325                 330                 335

Val Leu Met Asp Val Val His Ser His Ala Ser Asn Asn Val Thr Asp
            340                 345                 350

Gly Leu Asn Gly Tyr Asp Val Gly Gln Ser Thr Gln Glu Ser Tyr Phe
            355                 360                 365

His Ala Gly Asp Arg Gly Tyr His Lys Leu Trp Asp Ser Arg Leu Phe
            370                 375                 380

Asn Tyr Ala Asn Trp Glu Val Leu Arg Phe Leu Leu Ser Asn Leu Arg
385                 390                 395                 400

Tyr Trp Leu Asp Glu Phe Met Phe Asp Gly Phe Arg Phe Asp Gly Val
                405                 410                 415

Thr Ser Met Leu Tyr His His His Gly Ile Asn Val Gly Phe Thr Gly
            420                 425                 430

Asn Tyr Gln Glu Tyr Phe Ser Leu Asp Thr Ala Val Asp Ala Val Val
            435                 440                 445

Tyr Met Met Leu Ala Asn His Leu Met His Lys Leu Leu Pro Glu Ala
450                 455                 460

Thr Val Ala Glu Asp Val Ser Gly Met Pro Val Leu Cys Arg Pro
465                 470                 475                 480

Val Asp Glu Gly Gly Val Gly Phe Asp Tyr Arg Leu Ala Met Ala Ile
                485                 490                 495

Pro Asp Arg Trp Ile Asp Tyr Leu Lys Asn Lys Asp Asp Ser Glu Trp
                500                 505                 510

Ser Met Gly Glu Ile Ala His Thr Leu Thr Asn Arg Arg Tyr Thr Glu
            515                 520                 525

Lys Cys Ile Ala Tyr Ala Glu Ser His Asp Gln Ser Ile Val Gly Asp
            530                 535                 540

Lys Thr Ile Ala Phe Leu Leu Met Asp Lys Glu Met Tyr Thr Gly Met
545                 550                 555                 560

Ser Asp Leu Gln Pro Ala Ser Pro Thr Ile Asp Arg Gly Ile Ala Leu
                565                 570                 575

Gln Lys Met Ile His Phe Ile Thr Met Ala Leu Gly Gly Asp Gly Tyr
            580                 585                 590

Leu Asn Phe Met Gly Asn Glu Phe Gly His Pro Glu Trp Ile Asp Phe
            595                 600                 605

Pro Arg Glu Gly Asn Asn Trp Ser Tyr Asp Lys Cys Arg Arg Gln Trp
610                 615                 620
```

```
Ser Leu Val Asp Thr Asp His Leu Arg Tyr Lys Tyr Met Asn Ala Phe
625                 630                 635                 640

Asp Gln Ala Met Asn Ala Leu Asp Glu Arg Phe Ser Phe Leu Ser Ser
            645                 650                 655

Ser Lys Gln Ile Val Ser Asp Met Asn Asp Glu Glu Lys Val Ile Val
        660                 665                 670

Phe Glu Arg Gly Asp Leu Val Phe Val Phe Asn Phe His Pro Lys Lys
    675                 680                 685

Thr Tyr Glu Gly Tyr Lys Val Gly Cys Asp Leu Pro Gly Lys Tyr Arg
690                 695                 700

Val Ala Leu Asp Ser Asp Ala Leu Val Phe Gly His Gly Arg Val
705                 710                 715                 720

Gly His Asp Val Asp His Phe Thr Ser Pro Glu Gly Val Pro Gly Val
                725                 730                 735

Pro Glu Thr Asn Phe Asn Asn Arg Pro Asn Ser Phe Lys Val Leu Ser
            740                 745                 750

Pro Pro Arg Thr Cys Val Ala Tyr Tyr Arg Val Asp Glu Ala Gly Ala
        755                 760                 765

Gly Arg Arg Leu His Ala Lys Ala Glu Thr Gly Lys Thr Ser Pro Ala
    770                 775                 780

Glu Ser Ile Asp Val Lys Ala Ser Arg Ala Ser Ser Lys Glu Asp Lys
785                 790                 795                 800

Glu Ala Thr Ala Gly Gly Lys Lys Gly Trp Lys Phe Ala Arg Gln Pro
                805                 810                 815

Ser Asp Gln Asp Thr Lys
            820

<210> SEQ ID NO 10
<211> LENGTH: 814
<212> TYPE: PRT
<213> ORGANISM: Zea mays

<400> SEQUENCE: 10

Asp Leu Pro Ser Val Leu Phe Arg Arg Lys Asp Ala Phe Ser Arg Thr
1               5                   10                  15

Val Leu Ser Cys Ala Gly Ala Pro Gly Lys Val Leu Val Pro Gly Gly
            20                  25                  30

Gly Ser Asp Asp Leu Leu Ser Ser Ala Glu Pro Val Val Asp Thr Gln
        35                  40                  45

Pro Glu Glu Leu Gln Ile Pro Glu Ala Glu Leu Thr Val Glu Lys Thr
    50                  55                  60

Ser Ser Ser Pro Thr Gln Thr Thr Ser Ala Val Ala Glu Ala Ser Ser
65                  70                  75                  80

Gly Val Glu Ala Glu Glu Arg Pro Glu Leu Ser Glu Val Ile Gly Val
                85                  90                  95

Gly Gly Thr Gly Gly Thr Lys Ile Asp Gly Ala Gly Ile Lys Ala Lys
            100                 105                 110

Ala Pro Leu Val Glu Glu Lys Pro Arg Val Ile Pro Pro Gly Asp
    115                 120                 125

Gly Gln Arg Ile Tyr Glu Ile Asp Pro Met Leu Glu Gly Phe Arg Gly
130                 135                 140

His Leu Asp Tyr Arg Tyr Ser Glu Tyr Lys Arg Leu Arg Ala Ala Ile
145                 150                 155                 160

Asp Gln His Glu Gly Gly Leu Asp Ala Phe Ser Arg Gly Tyr Glu Lys
                165                 170                 175
```

```
Leu Gly Phe Thr Arg Ser Ala Glu Gly Ile Thr Tyr Arg Glu Trp Ala
            180                 185                 190

Pro Gly Ala Tyr Ser Ala Ala Leu Val Gly Asp Phe Asn Asn Trp Asn
        195                 200                 205

Pro Asn Ala Asp Ala Met Ala Arg Asn Glu Tyr Gly Val Trp Glu Ile
        210                 215                 220

Phe Leu Pro Asn Asn Ala Asp Gly Ser Pro Ala Ile Pro His Gly Ser
225                 230                 235                 240

Arg Val Lys Ile Arg Met Asp Thr Pro Ser Gly Val Lys Asp Ser Ile
            245                 250                 255

Pro Ala Trp Ile Lys Phe Ser Val Gln Ala Pro Gly Glu Ile Pro Tyr
            260                 265                 270

Asn Gly Ile Tyr Tyr Asp Pro Pro Glu Glu Lys Tyr Val Phe Lys
            275                 280                 285

His Pro Gln Pro Lys Arg Pro Lys Ser Leu Arg Ile Tyr Glu Ser His
            290                 295                 300

Val Gly Met Ser Ser Pro Glu Pro Lys Ile Asn Thr Tyr Ala Asn Phe
305                 310                 315                 320

Arg Asp Glu Val Leu Pro Arg Ile Lys Lys Leu Gly Tyr Asn Ala Val
                325                 330                 335

Gln Ile Met Ala Ile Gln Glu His Ser Tyr Tyr Ala Ser Phe Gly Tyr
            340                 345                 350

His Val Thr Asn Phe Phe Ala Pro Ser Ser Arg Phe Gly Thr Pro Glu
            355                 360                 365

Asp Leu Lys Ser Leu Ile Asp Lys Ala His Glu Leu Gly Leu Leu Val
        370                 375                 380

Leu Met Asp Ile Val His Ser His Ser Ser Asn Asn Thr Leu Asp Gly
385                 390                 395                 400

Leu Asn Gly Phe Asp Gly Thr Asp Thr His Tyr Phe His Gly Gly Pro
                405                 410                 415

Arg Gly His His Trp Met Trp Asp Ser Arg Leu Phe Asn Tyr Gly Ser
            420                 425                 430

Trp Glu Val Leu Arg Phe Leu Leu Ser Asn Ala Arg Trp Trp Leu Glu
            435                 440                 445

Glu Tyr Lys Phe Asp Gly Phe Arg Phe Asp Gly Val Thr Ser Met Met
        450                 455                 460

Tyr Thr His His Gly Leu Gln Val Thr Phe Thr Gly Asn Tyr Gly Glu
465                 470                 475                 480

Tyr Phe Gly Phe Ala Thr Asp Val Asp Ala Val Val Tyr Leu Met Leu
                485                 490                 495

Val Asn Asp Leu Ile Arg Gly Leu Tyr Pro Glu Ala Val Ser Ile Gly
            500                 505                 510

Glu Asp Val Ser Gly Met Pro Thr Phe Cys Ile Pro Val Gln Asp Gly
            515                 520                 525

Gly Val Gly Phe Asp Tyr Arg Leu His Met Ala Val Pro Asp Lys Trp
        530                 535                 540

Ile Glu Leu Leu Lys Gln Ser Asp Glu Tyr Trp Glu Met Gly Asp Ile
545                 550                 555                 560

Val His Thr Leu Thr Asn Arg Arg Trp Leu Glu Lys Cys Val Thr Tyr
            565                 570                 575

Cys Glu Ser His Asp Gln Ala Leu Val Gly Asp Lys Thr Ile Ala Phe
            580                 585                 590
```

```
Trp Leu Met Asp Lys Asp Met Tyr Asp Phe Met Ala Leu Asp Arg Pro
        595                 600                 605

Ser Thr Pro Arg Ile Asp Arg Gly Ile Ala Leu His Lys Met Ile Arg
        610                 615                 620

Leu Val Thr Met Gly Leu Gly Gly Glu Gly Tyr Leu Asn Phe Met Gly
625                 630                 635                 640

Asn Glu Phe Gly His Pro Glu Trp Ile Asp Phe Pro Arg Gly Pro Gln
                645                 650                 655

Ser Leu Pro Asn Gly Ser Val Ile Pro Gly Asn Asn Asn Ser Phe Asp
                660                 665                 670

Lys Cys Arg Arg Arg Phe Asp Leu Gly Asp Ala Asp Tyr Leu Arg Tyr
            675                 680                 685

Arg Gly Met Gln Glu Phe Asp Gln Ala Met Gln His Leu Glu Gly Lys
        690                 695                 700

Tyr Glu Phe Met Thr Ser Asp His Ser Tyr Val Ser Arg Lys His Glu
705                 710                 715                 720

Glu Asp Lys Val Ile Ile Phe Glu Arg Gly Asp Leu Val Phe Val Phe
                725                 730                 735

Asn Phe His Trp Ser Asn Ser Tyr Phe Asp Tyr Arg Val Gly Cys Phe
            740                 745                 750

Lys Pro Gly Lys Tyr Lys Ile Val Leu Asp Ser Asp Asp Gly Leu Phe
            755                 760                 765

Gly Gly Phe Ser Arg Leu Asp His Asp Ala Glu Tyr Phe Thr Ala Asp
        770                 775                 780

Trp Pro His Asp Asn Arg Pro Cys Ser Phe Ser Val Tyr Ala Pro Ser
785                 790                 795                 800

Arg Thr Ala Val Val Tyr Ala Pro Ala Gly Ala Glu Asp Glu
                805                 810
```

TRANSGENIC PLANTS SYNTHESIZING HIGH AMYLOSE STARCH

FIELD OF THE INVENTION

The present invention relates to genetically modified plant cells and plants wherein the genetic modification leads to the reduction of the activity of R1 and BEI and BEII proteins in comparison with corresponding plant cells of wild type plants that have not been genetically modified. Furthermore, the present invention relates to means and methods for the production thereof. Plant cells and plants of that type synthesise a modified starch characterised in that it has an amylose content of at least 75% and—in comparison with starch of corresponding wild type plants which have not been genetically modified—a reduced phosphate content and/or a modified distribution of the side chains and/or an increased gel strength in the texture analyser and/or a modified starch granule morphology and/or a modified average starch granule size. Thus, the present invention also relates to starch that can be synthesised by the plant cells and plants of the invention as well as methods for the production of this starch.

With regard to the increasing importance of plant ingredients as renewable raw material sources in the past few years, one of the problems of research in the field of biotechnology is to endeavour adjustment of these raw materials to the requirements of the processing industry. For allowing an application of renewable raw materials in as many as fields as possible, it is furthermore necessary to achieve a great variety of substances.

Apart from oils, fats and proteins, polysaccharides represent the essential renewable raw materials from plants. Among the polysaccharides, starch plays a central role beside cellulose. It is one of the most important storage substances in higher plants. For allowing as wide an application of starch as possible, it seems desirable to provide plants which are able to synthesise modified starch that is particularly suitable for different purposes. One possibility of providing such plants is—apart from cultivating—the purposeful genetic modification of the starch metabolism of starch-producing plants by genetic engineering.

The polysaccharide starch is a polymer of chemically uniform basic building blocks—the glucose molecules. It is, however, a very complex mixture of different molecule forms which differ with regard to their polymerisation degree and the occurrence of branchings of the glucose chains. Thus, starch is not a uniform raw material. There are two chemically different components of starch: the amylose and the amylopectin. In plants typically used for the production of starch, such as e.g. maize, wheat or potato, the synthesised starch consists of about 20%–30% of amylose starch and of about 70%–80% of amylopectin starch.

Amylose was considered a linear polymer for a long time, consisting of α-1,4-glycosidically bound α-D-glucose monomers. In recent studies, however, the presence of about 0.1% α-1,6-glycosidic branching points has been proven (Hizukuri and Takagi, Carbohydr. Res. 134, (1984), 1–10; Takeda et al., Carbohydr. Res. 132, (1984), 83–92).

As a rule, the complete separation of the amylose from the amylopectin is very difficult so that the quality of the amylose strongly depends on the type of the separation method chosen.

There are different methods for the determination of the amylose content. Some of these methods are based on the iodine-binding capacity of the amylose which can be determined potentiometrically (Banks & Greenwood, in W. Banks & C. T. Greenwood, Starch and its components (page 51–66), Edinburgh, Edinburgh University Press), amperometrically (Larson et al., Analytical Chemistry 25(5), (1953), 802–804) or spectrophotometrically (Morrison & Laignelet, J. Cereal Sc. 1, (1983), 9–20). The determination of the amylose content can also be carried out calorimetrically by means of DSC (differential scanning calorimetry) measurements (Kugimiya & Donovan, Journal of Food Science 46, (1981), 765–770; Sievert & Holm, Starch/Stärke 45 (4), (1993), 136–139). Moreover, it is possible to determine the amylose content by using the SEC (size exclusion chromatography) of native or debranched starch. This method was particularly recommended for the determination of the amylose content of genetically modified starches (Gérard et al., Carbohydrate Polymers 44, (2001), 19–27).

The choice of the analysis method used for the determination of the amylose content of a starch has a crucial influence on the size of the amylose figures determined as could be shown by various studies (Shi et al., J. Cereal Science 27, (1998), 289–299; Gérard et al., Carbohydrate Polymers 44, (2001), 19–27).

In contrast to the amylose, the amylopectin is branched to a larger degree and exhibits about 4% branching points which occur due to the presence of additional α-1,6-glycosidic linkings. The amylopectin is a complex mixture of glucose chains branched differently.

A further essential difference between amylose and amylopectin is the molecular weight. While amylose—depending on the origin of the starch—has a molecular weight of $5 \times 10^5$–$10^6$ Da, the molecular weight of amylopectin is between $10^7$ and $10^8$ Da. Both macromolecules can be differentiated from each other by their molecular weight and their different physico-chemical properties, which can be made apparent in the simplest way by their different iodine-binding properties.

The functional properties of the starch are strongly influenced—apart from the amylose/amylopectin ratio and the phosphate content—by the molecular weight, the pattern of the side chain distribution, the content of ions, the lipid and protein content, the average starch granule size and the starch granule morphology etc. Important functional properties to be mentioned are, for example, the solubility, the retrogradation behaviour, the water binding capacity, the film formation properties, the viscosity, the pasting properties, the freeze-thaw-stability, the acid stability, the gel strength etc. The starch granule size, too, can be important for different applications.

The ratio of amylopectin and amylose has a strong influence on the physico-chemical properties of the starches and, thus, on the possible applications of these starches. Since methods for the separation of these two components are very time-consuming and costly, such methods are no longer used on a large technical scale (Yound, A. H. in: Starch Chemistry and Technology. Eds. R. L. Whistler, J. N. BeMiller and E. F. Paschall. Academic Press, New York, 1984, 249–283). For a plurality of applications it would be desirable to have starches at disposal which still contain only one of the two polymers or at least one of the two starch components in an enriched form.

So far, both mutants and plants produced by genetic engineering have been described which, in comparison with corresponding wild type plants, exhibit a modified amylopectin/amylose ratio.

For example, the so-called "waxy" mutant from maize exhibiting a mutation in the gene encoding the starch granule bound starch synthase I (abbreviated: GBSSI) (Akasuka and Nelson, J. Biol. Chem., 241, (1966), 2280–2285;

Shure et al., Cell 35 (1983), 225–233), produces a starch essentially consisting of amylopectin. For potato, genotypes were produced both by means of chemical mutagenesis of a haploid line (Hovenkamp-Hermelink et al., Theor. Appl. Genet., 225, (1987), 217–221) and by means of antisense inhibition of the GBSSI-gene, whose starches essentially consist of amylopectin starch. In comparison with starches of the corresponding wild type plants, such waxy potato starches do not exhibit any differences with regard to phophate content, the morphology of the starch granule or the ion content (Visser et al., Starch/Stärke, 49, (1997), 438–443).

Furthermore, maize mutants are commercially available which exhibit starches with amylose contents of about 50% or about 70% (amylose content determined by potentiometric determination of the iodine-binding capacity) and which are designated Hylon V® or HylonVII® (National Starch and Chemical Company, Bridgewater, N.J., U.S.A.). Moreover, also maize hybrids have been described which synthesise so-called "low amylopectin starch" (LAPS) and exhibit a content of high molecular ("high mol weight") amylopectin of about 2.5% and an amylose content of about 90% (potentiometric determination of the iodine-binding capacity) (Shi et al., J. Cereal Science 27, (1998), 289–299).

Furthermore, transgenic potato plants have been described which, due to the antisense-inhibition of the branching enzyme I (=BEI) and the branching enzyme II (=BEII) gene, synthesise a potato starch which exhibits an amylose content of up to 75% by colorimetric determination of the amylose content according to the method described by Morrison and Laignelet (J. Cereal Sci. 1, (1983), 9–20) (Schwall et al., Nature Biotechn. 18, (2000), 551–554). These potato starches are characterised by a phosphate content of the starch which is up to 6 times higher compared to corresponding wild type plants. Furthermore, the international patent application WO 97/11188 describes transgenic potato plants which, due to their antisense inhibition of the R1 gene and the BEI gene synthesise a starch with an amylose content of more than 70%, the amylose content having been determined according to the method by Hovenkamp & Hermelink (Potato Research 31, (1988), 241–246).

Transgenic potato plant cells and potato plants synthesising a starch having an amylose content of more than 75% (calorimetric determination of the amylose content according to Hovenkamp & Hermelink (Potato Research 31, (1988), 241–246) and, at the same time, a reduced phosphate content in comparison with corresponding wild type plants have not been described in the state of the art so far. The same applies to the potato starches that can be isolated from these potato plant cells and plants and to methods for the production of such starches. However, the provision of such starches is desirable since their physico-chemical properties can be expected to be advantageously useful for various industrial applications.

Thus, the technical problem underlying the present invention is to provide plant cells and plants synthesising starch which has an amylose content of more than 75% (calorimetric determination of the amylose content according to Hovenkamp & Hermelink (Potato Research 31, (1988), 241–246) and a reduced phosphate content in comparison with the phosphate content of starch from corresponding wild type plant cells and plants that have not been genetically modified, as well as to provide such starch which differs from the starches described in the state of the art in its structural and/or functional properties and is, thus, more suitable for general and/or specific purposes.

This technical problem has been solved by providing the embodiments characterised in the claims.

SUMMARY OF THE INVENTION

Thus, the present invention relates to a transgenic plant cell which is genetically modified, wherein the genetic modification leads to a reduction of the activity of one or more R1 proteins occurring endogenously in the plant cell and to the reduction of the activity of one or more BEI proteins occurring endogenously in the plant cell and to the reduction of the activity of one or more BEII proteins occurring endogenously in the plant cell in comparison with corresponding plant cells of wild type plants, the cells not being genetically modified.

The genetic modification may be any genetic modification leading to a reduction of the activity of one or more R1 proteins occurring endogenously in the plant cell and to the reduction of the activity of one or more BEI proteins occurring endogenously in the plant cell and to the reduction of the activity of one or more BEII proteins occurring endogenously in the plant cell in comparison with corresponding plant cells of wild type plants, the cells not being genetically modified.

In this context, the term "transgenic" means that the plant cells of the invention differ in their genetic information from corresponding plant cells which are not genetically modified due to a genetic modification, in particular the introduction of one or more foreign nucleic acid molecules.

In this context, the term "genetically modified" means that the plant cell is modified in its genetic information due to the introduction of one or more foreign nucleic acid molecules and that the presence and/or the expression of the foreign nucleic acid molecule/s lead/s to a phenotypic modification. In this context, phenotypic modification preferably relates to a measurable modification of one or more functions of the cells. Genetically modified plants cells of the invention, for example, exhibit a reduction of the expression of one or more R1 genes occurring endogenously in the plant cell and a reduction of the expression of one or more BEI genes occurring endogenously in the plant cell and a reduction of the expression of one or more BEII genes occurring endogenously in the plant cell in comparison with corresponding plant cells of wild type plants, the cells not being genetically modified, and/or a reduction of the activity of one or more R1 proteins occurring endogenously in the plant cell and a reduction of the activity of one or more BEI proteins occurring endogenously in the plant cell and a reduction of the activity of one or more BEII proteins occurring endogenously in the plant cell in comparison with corresponding plant cells of wild type plants, the cells not being genetically modified.

Within the meaning of the present invention, the term "reduction of the activity" means a reduction of the expression of endogenous genes encoding R1, BEI and/or BEII proteins and/or a reduction of the amount of R1, BEI and/or BEII proteins in the cells and/or a reduction of the enzymatic activity of the R1, BEI and/or BEII proteins in the cells.

In the context of the present invention, the term "reduction of expression" refers to a reduction of the amount of transcripts of the respective endogenous gene in a plant cell of the invention as compared to a corresponding wild-type plant cell. The reduction of the expression can, for instance, be determined by measuring the amount of transcripts encoding R1, BEI or BEII proteins, e.g. by means of Northern blot analysis or RT-PCR. In this context, a reduction preferably means a reduction of the amount of transcripts in comparison with corresponding cells that have not been genetically modified by at least 50%, in particular by at least 70%, more preferably by at least 85% and most preferably by at least 95%.

The reduction of the amount of R1, BEI and/or BEII proteins can, for instance, be determined by means of Western blot analysis. In this context, a reduction preferably means a reduction of the amount of R1, BEI and/or BEII proteins in comparison with corresponding cells which have not been genetically modified by at least 50%, in particular by at least 70%, more preferably by at least 85% and most preferably by at least 95%.

Methods for determining the reduction of the enzymatic activity of the R1, BEI and BEII proteins are known to the person skilled in the art and will be described further below for each protein individually. In the context of the present invention, the term "R1 protein" relates to proteins which have been described, for example, in Lorberth et al. (Nature Biotech. 16, (1998), 473–477) and in the international patent applications WO 98/27212, WO 00/77229, WO 00/28052 and which have the following characteristics. Important characteristics of R1 proteins are i) their amino acid sequence (see, for example, GenBank Acc. No. A61831, Y09533); ii) their localisation in the plastides of plant cells; iii) their ability to influence the degree of phosphorylation of starch in plants.

Further, the term "R1 protein" refers to a protein catalysing the phosphorylation of starch in dikinase-type reaction in which three substrates, an a-polyglucan, ATP and $H_2O$ are converted into three products, an a-polyglucan-P, AMP and orthophosphate (Ritte et al., PNAS 99(10) (2002), 7166–7171).

The inhibition of the R1 gene encoding an R1 protein from potato in transgenic potato plants, for example, leads to a reduction of the phosphate content of the starch which can be isolated from the potato tuber. Moreover, Lorberth et al. were able to demonstrate that the R1 protein from *Solanum tuberosum* is able to phosphorylate bacterial glycogen when the corresponding R1 cDNA is expressed in *E. coli* (Lorberth et al., Nature Biotech. 16, (1998), 473–477).

Ritte et al. (Plant J. 21, (2000), 387–391) were able to show that the R1 protein from *Solanum tuberosum* in potato plants binds to starch granules in a reversible way, wherein the strength of the binding to the starch granule depends on the metabolic status of the plant. In potato plants, the protein is mainly present in starch granule bound form in leaves that have been kept in the dark. After exposing the leaves to light, however, the protein is mainly present in the soluble form which is not bound to the starch granule.

Furthermore, the inhibition of the expression of the R1 gene from potato in transgenic potato plants or in the tubers thereof leads to a reduction of the so-called "cold-induced-sweetenings" (Lorberth et al., Nature Biotech. 16, (1998), 473–477).

In the context of the present invention, the term "R1 protein" also relates to proteins which exhibit a significant homology (identity) of at least 60%, preferably of at least 80%, more preferably of at least 90% to the amino acid sequence stated under SEQ ID NO: 6 or under the GenBank Acc. No. Y09533 or A61831, and which are able to modify the degree of phosphorylation of polysaccharides such as, for example, starch and/or glycogen. Preferably, the R1 protein originates from potato (GenBank Acc. No. Y09533 or A61831).

Preferably, an R1 protein, as addressed in the embodiments of the present invention, is encoded by a nucleic acid molecule which hybridises, advantageously under stringent conditions, with the nucleic acid molecule having the nucleotide sequences shown under SEQ ID NO: 5 and which encodes a polypeptide having the activity of an R1 protein.

Within the present invention the term "hybridization" means hybridization under conventional hybridization conditions (also referred to as "low stringency conditions"), preferably under stringent conditions (also referred to as "high stringency conditions"), as for instance described in Sambrook and Russell (2001), Molecular Cloning, A Laboratory Manual, CSH Press, Cold Spring Harbour, N.Y., U.S.A. Within an especially preferred meaning the term "hybridization" means that hybridization occurs under the following conditions:

Hybridization buffer: 2×SSC; 10× Denhardt solution (Fikoll 400+PEG+BSA; ratio 1:1:1); 0.1% SDS; 5 mM EDTA; 50 mM $Na_2HPO_{4;\ 250}$ µg/ml of herring sperm DNA; 50 µg/ml of tRNA; or
0.25 M of sodium phosphate buffer, pH 7.2;
1 mM EDTA
7% SDS
Hybridization temperature T=60° C.
Washing buffer: 2×SSC; 0.1% SDS
Washing temperature T=60° C.

Nucleic acid molecules which hybridize with a nucleic acid molecule having the nucleotide sequence shown under SEQ ID NO: 5 can, in principle, encode a R1 protein from any organism expressing such a protein.

Such hybridizing nucleic acid molecules can for instance be isolated from genomic libraries or cDNA libraries of plants. Alternatively, they can be prepared by genetic engineering or chemical synthesis.

Such nucleic acid molecules may be identified and isolated with the use of a nucleic acid molecule encoding an R1 protein as disclosed herein or parts of such a molecule or reverse complements of such a molecule, for instance by hybridization according to standard methods (see for instance Sambrook and Russell (2001), Molecular Cloning. A Laboratory Manual, CSH Press, Cold Spring Harbor, N.Y., U.S.A).

Nucleic acid molecules possessing the same or substantially the same nucleotide sequence as indicated in SEQ ID NO: 5 or parts thereof can, for instance, be used as hybridization probes. The fragments used as hybridization probes can also be synthetic fragments which are prepared by usual synthesis techniques, and the sequence of which substantially coincides with that of a nucleic acid molecule specifically described herein.

The hybridizing nucleic acid molecules also comprise fragments, derivatives and allelic variants of the nucleic acid molecule having the nucleotide sequence shown under SEQ ID NO: 5. Herein, fragments are understood to mean parts of the nucleic acid molecules which are long enough to encode an R1 protein. In this connection, the term derivative means that the sequences of these nucleic acid molecules differ from the sequence of an above-described nucleic acid molecule in one or more positions and show a high degree of homology to such a sequence. In this context, homology means a sequence identity of at least 40%, in particular an identity of at least 60%, preferably of at least 65%, more preferably of at least 70%, even more preferably of at least 80%, in particular of at least 85%, furthermore preferred of at least 90% and particularly preferred of at least 95%. Most preferably homology means a sequence identity of at least n %, wherein n is an integer between 40 and 100, i.e. $40 \leq n \leq 100$. Deviations from the above-described nucleic acid molecules may have been produced, e.g., by deletion, substitution, insertion and/or recombination.

Preferably, the degree of homology is determined by comparing the respective sequence with the nucleotide sequence of the coding region of SEQ ID No: 5. When the sequences which are compared do not have the same length, the degree of homology preferably refers to the percentage of nucleotide residues in the shorter sequence which are identical to nucleotide residues in the longer sequence. The degree of homology can be determined conventionally using known computer programs such as the ClustalW program (Thompson et al., Nucleic Acids Research 22 (1994), 4673–4680) distributed by Julie Thompson (Thompson@EMBL-Heidelberg.DE) and Toby Gibson (Gibson@EMBL-Heidelberg.DE) at the European Molecular Biology Laboratory, Meyerhofstrasse 1, D 69117 Heidelberg, Germany. ClustalW can also be downloaded from several websites including IGBMC (Institut de Génétique et de Biologie Moléculaire et Cellulaire, B.P. 163, 67404 Illkirch Cedex, France; ftp://ftp-igbmc.u-strasbg.fr/pub/) and EBI (ftp://ftp.ebi.ac.uk/pub/software/) and all sites with mirrors to the EBI (European Bioinformatics Institute, Wellcome Trust Genome Campus, Hinxton, Cambridge CB10 1SD, UK).

When using ClustalW program version 1.8 to determine whether a particular sequence is, for instance, 90% identical to a reference sequence according to the present invention, the settings are set in the following way for DNA sequence alignments:
KTUPLE=2, TOPDIAGS=4, PAIRGAP=5, DNAMATRIX: IUB, GAPOPEN=10, GAPEXT=5, MAXDIV=40, TRANSITIONS: unweighted.

For protein sequence alignments using ClustalW program version 1.8 the settings are the following: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS(OFF), NOPGAP, NOHGAP.

Homology, moreover, means that there is a functional and/or structural equivalence between the corresponding nucleic acid molecules or proteins encoded thereby. Nucleic acid molecules which are homologous to one of the above-described molecules and represent derivatives of these molecules are generally variations of these molecules which represent modifications having the same biological function. They may be either naturally occurring variations, for instance sequences from other microorganisms, or mutations, and said mutations may have formed naturally or may have been produced by deliberate mutagenesis. Furthermore, the variations may be synthetically produced sequences. The allelic variants may, e.g., be naturally occurring variants or synthetically produced variants or variants produced by recombinant DNA techniques.

The proteins encoded by the different variants of the nucleic acid molecule having the nucleotide sequence shown under SEQ ID NO: 5 possess certain characteristics they have in common. These include for instance enzymatic activity, molecular weight, immunological reactivity, conformation, etc., and physical properties, such as for instance the migration behavior in gel electrophoreses, chromatographic behavior, sedimentation coefficients, solubility, spectroscopic properties, stability, pH optimum, temperature optimum etc.

In the context of the present invention, the term "R1 gene" relates to a nucleic acid molecule (e.g. cDNA, DNA) encoding an "R1 protein" as described above. Nucleic acid molecules encoding R1 proteins have been described for various plants such as, e.g. maize (WO 98/27212 A1), rice (WO 00/28052 A1) and wheat (WO 00/77229 A1). Preferably, the R1 gene originates from potato, an R1 cDNA from potato with the nucleotide sequence stated under SEQ ID NO: 5 or GenBank Acc. No. Y09533 or A61831 is particularly preferred.

In the context of the present invention, the term "branching enzyme" or "BE protein" ($\alpha$-1,4-glucan: $\alpha$-1,4-glucan 6-glycosyltransferase, E.C. 2.4.1.18) relates to a protein catalysing a transglycosylation reaction, wherein ($\alpha$-1,4-linkings of an $\alpha$-1,4-glucan donor are hydrolysed and the $\alpha$-1,4-glucan chains released thereby are transferred to an $\alpha$-1,4-glucan acceptor chain and are thereby converted into $\alpha$-1,6-linkings. Within the meaning of the present invention, the term "BE gene" is a gene encoding a "BE protein".

In the context of the present invention, the term "BEI protein" relates to a branching enzyme (=BE) of the isoform I, preferably the BEI protein originates from potato plants.

The designation of the isoforms follows the nomenclature suggested by Smith-White and Preiss (Smith-White and Preiss, Plant Mol. Biol. Rep. 12 (1994), 67–71; Larsson et al., Plant Mol. Biol. 37, (1998), 505–511). This nomenclature assumes that all branching enzymes exhibiting a higher homology (identity) on the amino acid level to the BEI protein from maize having the amino acid sequence shown under SEQ ID NO: 9 (GenBank Acc. No. D11081; Baba et al., Biochem. Biophys. Res. Commun. 181 (1), (1991), 87–94; Kim et al., Gene 216, (1998), 233–243) than to the BEII protein from maize having the amino acid sequence shown under SEQ ID NO: 10 (GenBank Acc. No. AF072725, U65948) are designated branching enzymes of the isoform I or, in short, BEI proteins.

In the context of the present invention, the term "BEI gene" relates to a nucleic acid molecule (e.g. cDNA, DNA) encoding a "BEI protein", preferably a BEI protein from potato plants. Such nucleic acid molecules have been described for numerous plants, for example for maize (GenBank Acc. No. D11081, AF 072724), rice (GenBank Acc. No. D11082), pea (GenBank Acc. No. X80010) and potato. Different forms of the BEI gene or the BEI protein from potato have been described, for example, by Khoshnoodi et al. (Eur. J. Biochem. 242 (1) (1996), 148–155), GenBank Acc. No. Y08786 and by Kossmann et al. (Mol. Gen. Genet. 230 (1991), 39–44). In potato plants, the BEI gene is expressed mainly in the tubers and hardly in the leaves (Larsson et al., Plant Mol. Biol. 37, (1998), 505–511).

Preferably, a BEI protein, as addressed in the embodiments of the present invention, is encoded by a nucleic acid molecule which hybridises, advantageously under stringent conditions, with the nucleic acid molecule having the nucleotide sequence shown under SEQ ID NO: 7 and which encodes a polypeptide having branching enzyme activity.

The definition for the term "hybridisation" as defined above in connection with R1 proteins applies equally for the definition of nucleic acid molecules hybridising with the nucleic acid molecule having the nucleotide sequence of SEQ ID NO: 7. Preferably, a BEI protein as referred to herein displays a sequence identity of at least 60%, in particular of at least 75%, preferably of at least 85%, more preferably at least 90% and even more preferably at least 95% to the amino acid sequence depicted under SEQ ID NO: 8.

In the context of the present invention, the term "BEII protein" relates to a branching enzyme (=BE) of the isoform II, preferably it originates from potato plants. Within the meaning of the present invention, all enzymes exhibiting a higher homology (identity) on the amino acid level to the BEII protein from maize (GenBank Acc. No. AF072725, U65948) than to the BEI protein from maize (GenBank Acc. No. D 11081, AF 072724) are to be designated BEII protein.

In the context of the present invention, the term "BEII gene" relates to a nucleic acid molecule (e.g. cDNA, DNA) encoding a "BEII protein", preferably a BEII protein from potato plants. Such nucleic acid molecules have been described for numerous plants, for example, for potato (GenBank Acc. No. AJ00004, AJ011888, AJ011889, AJ011885, AJ011890), maize (AF072725, U65948), barley (AF064561), rice (D16201) and wheat (AF286319). In potato plants, the BEII gene is expressed mainly in the leaves and hardly in the tubers (Larsson et al., Plant Mol. Biol. 37, (1998), 505–511).

Preferably, a BEII protein, as addressed in the embodiments of the present invention, is encoded by a nucleic acid molecule which hybridises, advantageously under stringent conditions, with the nucleic acid molecule having the nucleotide sequence shown under SEQ ID NO: 9 and which encodes a polypeptide having branching enzyme activity.

The definition for the term "hybridisation" as defined above in connection with R1 proteins applies equally for the definition of nucleic acid molecules hybridising with the nucleic acid molecule having the nucleotide sequence of SEQ ID NO: 3. Preferably, a BEII protein as referred to herein displays a sequence identity of at least 60%, in particular of at least 75%, preferably of at least 85%, more preferably at least 90% and even more preferably at least 95% to the amino acid sequence depicted under SEQ ID NO: 4.

In a preferred embodiment of the present invention, the genetic modification of the transgenic plant cell of the invention is the introduction of one or more foreign nucleic acid molecules the presence and/or expression of which leads to a reduction of the activity of R1 and BEI and BEII proteins in comparison with corresponding plant cells of wild type plants, the cells not being genetically modified.

Preferably, this reduction of activity is achieved by inhibiting the expression of the endogenous genes encoding R1 proteins, BEI proteins and BEII proteins.

The production of the plant cells of the invention can be achieved by different methods known to the person skilled in the art, e.g. by methods leading to an inhibition of the expression of endogenous genes encoding an R1, BEI or BEII protein. These include, for example, the expression of a corresponding antisense RNA, the provision of molecules or vectors mediating a co-suppression effect, the expression of a ribozyme constructed accordingly which specifically cleaves transcripts encoding an R1, BEI or BEII protein or the so-called "in-vivo mutagenesis". Furthermore, the reduction of the R1 and/or the BEI and/or the BEII activity in the plant cells may also be caused by the simultaneous expression of sense and antisense RNA molecules of the target gene to be repressed, preferably of the R1 and/or the BEI and/or the BEII gene, a technique which is commonly referred to as RNA interference (RNAi) (Bosher and Labouesse, Nature Cell Biology 2, (2000), E31–E36; Waterhouse et al., PNAS 95, (1998), 13959–13964). Furthermore, by the use of double-stranded RNA molecules comprising promoter sequences, a transcriptional inactivation of the promoter can be achieved. These and further methods for reducing the activity of proteins will be described in more detail below. All these methods are based on the introduction of one or more foreign nucleic acid molecules into the genome of plant cells.

Within the context of the present invention, the term "foreign nucleic acid molecule" is understood to be a molecule which either does not occur naturally in corresponding plant cells or which does not occur naturally in the plant cells in the concrete spatial order or which is located at a position in the genome of the plant cell at which it does not occur naturally. The foreign nucleic acid molecule preferably is a recombinant molecule which consists of various elements the combination or specific spatial order of which does not occur naturally in plant cells.

The foreign nucleic acid molecule can, for instance, be a so-called "triple construct" which is understood to be a single vector for plant transformation which contains both the genetic information for inhibiting the expression of one or more endogenous R1 genes and for inhibiting the expression of one or more BEI and BEII genes or the presence or expression of which leads to the reduction of the activity of one or more R1, BEI and BEII proteins.

In another embodiment, the foreign nucleic acid molecule may be a so-called "double construct" which is understood to be a vector for plant transformation which contains the genetic information for inhibiting the expression of two of the three target genes (R1, BEI, BEII gene) or the presence or expression of which leads to the reduction of the activity of two of the three target proteins (R1, BEI, BEII proteins). In this embodiment of the invention, the inhibition of the expression of the third target gene and/or the reduction of the activity of the third target protein takes place by means of a separate foreign nucleic acid molecule which contains the corresponding genetic information for exerting this inhibiting effect.

In another embodiment of the invention, it is not a triple construct that is introduced into the genome of the plant cell but several different foreign nucleic acid molecules, one of these foreign nucleic acid molecules being for example a DNA molecule which, for instance, is a co-suppression construct leading to a reduction of the expression of one or more endogenous R1 genes, and a further foreign nucleic acid molecule being a DNA molecule encoding, for example, an antisense RNA leading to a reduction of the expression of one or more endogenous BEI and/or BEII genes. In principle, as regards the construction of the foreign nucleic acid molecules, it is also suitable to use every combination of antisense, co-suppression and ribozyme constructs or in-vivo mutagenesis, which all lead to a simultaneous reduction of the gene expression of endogenous genes encoding one or more R1, BEI and BEII proteins or which lead to a simultaneous reduction of the activity of one or more R1, BEI and BEII proteins.

In this case, the foreign nucleic acid molecules can be introduced simultaneously ("co-transformation") or consecutively, i.e. one after the other ("super transformation"), into the genome of the plant cell.

In another embodiment of the invention, at least one antisense RNA is expressed for reducing the activity of one or more R1 proteins and/or BEI proteins and/or BEII proteins in plant cells.

For inhibiting the gene expression by means of antisense or co-suppression technology, it is possible to use for instance a DNA molecule which comprises the entire sequence encoding an R1 and/or BEI and/or BEII protein, including flanking sequences that may optionally be present, as well as DNA molecules which only comprise parts of the coding sequence and/or flanking sequences, wherein these parts must be long enough to lead to an antisense effect or a co-suppression effect in the cells. In general, sequences having a minimum length of 15 bp, preferably a length of 100 to 500 bp, in particular sequences having a length of more than 500 bp, are suitable for an efficient antisense or co-suppression inhibition. Usually, DNA molecules which are shorter than 5000 bp, preferably sequences which are shorter than 2500 bp are used.

For antisense or co-suppression approaches, it is also suitable to use DNA sequences which have a high degree of homology to the sequences that occur endogenously in the plant cell and that encode R1, BEI or BEII proteins. The minimum degree of homology should be higher than 65%. It is preferred to use sequences having a homology of at least 90%, in particular between 95 and 100%.

Moreover, also introns, i.e. of non-coding regions of genes encoding R1, BEI and/or BEII proteins, are conceivable for use to achieve an antisense or a co-suppressive effect.

The use of intron sequences for inhibiting the gene expression of genes encoding proteins of the starch biosynthesis has been described in the international patent applications WO 97/04112, WO 97/04113, WO 98/37213, WO 98/37214.

The person skilled in the art knows how to achieve an antisense and a co-suppressive effect. The method of co-suppression inhibition was described, for instance, in Jorgensen (Trends Biotechnol. 8 (1990), 340–344), Niebel et al. (Curr. Top. Microbiol. Immunol. 197 (1995), 91–103), Flavell et al. (Curr. Top. Microbiol. Immunol. 197 (1995), 43–46), Palaqui and Vaucheret (Plant. Mol. Biol. 29 (1995, 149–159), Vaucheret et al. (Mol. Gen. Genet. 248 (1995), 311–317), de Borne et al. (Mol. Gen. Genet. 243 (1994), 613–621).

The skilled persons are also familiar with the expression of ribozymes for reducing the activity of certain enzymes in cells and is described, for example, in EP-B1 0 321 201. The expression of ribozymes in plant cells has been described, for instance, in Feyter et al. (Mol. Gen. Genet. 250, (1996), 329–338).

Furthermore, the R1 and/or BEI and/or BEII activity in plant cells may also be reduced by the so-called "in-vivo mutagenesis" in which a hybrid RNA-DNA oligonucleotide ("chimeroplast") is introduced into cells by means of the transformation of cells (Kipp, P. B. et al., Poster at the 5$^{th}$ International Congress of Plant Molecular Biology, 21–27September 1997, Singapore; R. A. Dixon and C. J. Arntzen, Meeting report to "Metabolic Engineering in Transgenic Plants", Keystone Symposia, Copper Mountain, Colo., U.S.A., TIBTECH 15, (1997), 441–447; international patent application WO 95/15972; Kren et al., Hepatology 25, (1997), 1462–1468; Cole-Strauss et al., Science 273, (1996), 1386–1389).

A part of the DNA component of the RNA-DNA oligonucleotide is homologous to a nucleic acid sequence of an endogenous R1, BEI and/or BEII gene, it has, however, a mutation in comparison with an endogenous R1, BEI and/or BEII gene or it contains a heterologous region which is embraced by the homologous regions.

It is possible to transfer the mutation or heterologous region contained in the DNA component of the RNA-DNA molecule into the genome of a plant cell by means of base pairing of the homologous regions of the RNA-DNA oligonucleotide and the endogenous nucleic acid molecule, followed by homologous recombination. As a result, the activity of one or more R1, BEI and/or BEII proteins is reduced.

In addition, the reduction of the R1 and/or BEI and/or BEII activity in the plant cells may also be caused by the simultaneous expression of sense and antisense RNA molecules of the target gene that is to be repressed, preferably of the R1 and/or the BEI and/or the BEII gene.

This can be achieved, for instance, by using chimeric constructs which contain inverted repeats of the respective target gene or of parts of the target gene. In this case, the chimeric constructs encode sense and antisense RNA molecules of the respective target gene. Sense and antisense RNA are synthesised simultaneously in planta as one RNA molecule, wherein the sense and the antisense RNA may be separated from each other by a spacer and form a double-stranded RNA-molecule. It was possible to show that the introduction of inverted repeat DNA constructs into the genome of plants is a very efficient method for repressing the genes corresponding to the inverted repeat DNA constructs (Waterhouse et al., Proc. Natl. Acad. Sci. USA 95, (1998), 13959–13964; Wang and Waterhouse, Plant Mol. Biol. 43, (2000), 67–82; Singh et al., Biochemical Society Transactions vol. 28, part 6 (2000), 925–927; Liu et al., Biochemical Society Transactions vol. 28, part 6 (2000); 927–929; Smith et al., Nature 407, (2000), 319–320; international patent application WO 99/53050 A1). Sense and antisense sequences of the target gene or of the target genes can also be expressed separately using the same or different promoters (Nap, J.-P. et al., 6$^{th}$ International Congress of Plant Molecular Biology, Quebec, 18–24 June 2000; Poster S7-27, lecture session S7).

Thus, it is also possible to reduce the R1 and/or BEI and/or BEII activity in the plant cells by the production of double-stranded RNA molecules of R1 and/or BEI and/or BEII genes. Preferably, inverted repeats of DNA molecules of R1 and/or BEI and/or BEII genes or cDNAs are introduced into the genome of plants for this purpose, wherein the DNA molecules to be transcribed (R1, BEI or BEII gene or cDNA or fragments of these genes or cDNAs) are under the control of a promoter which controls the expression of said DNA molecules.

Furthermore, it is known that in planta the formation of double-stranded RNA molecules of promoter DNA molecules in plants can lead in trans to a methylation and a transcriptional inactivation of homologous copies of these promoters which are called target promoters in the following (Mette et al., EMBO J. 19, (2000), 5194–5201).

Therefore, it is possible to reduce the gene expression of a certain target gene (e.g. R1, BEI or BEII gene) by means of the inactivation of the target promoter, the target gene being naturally controlled by this target promoter.

This means that, in this case, in contrast to the original function of promoters in plants, the DNA molecules which comprise the target promoters of the genes to be repressed (target genes) are not used as control elements for the expression of genes or cDNAs but as transcribable DNA molecules themselves.

For producing the double-stranded target promoter RNA molecules in planta which may be present there as RNA hairpin molecules, constructs are preferred to be used which contain inverted repeats of the target promoter DNA molecule, the target promoter DNA molecules being under the control of a promoter which controls the gene expression of said target promoter DNA molecules.

Then, these constructs are introduced into the genome of plants. The expression of the inverted repeats of said target promoter DNA molecules leads to the formation of double-stranded target promoter RNA molecules in planta (Mette at el., EMBO J. 19, (2000), 5194–5201). In this way, it is possible to inactivate the target promoter.

Therefore, the R1 and/or BEI and/or BEII activity in the plant cells can also be reduced by generating double-stranded RNA molecules of promoter sequences of R1 and/or BEI and/or BEII genes. For this purpose, inverted repeats of promoter DNA molecules of R1 and/or BEI and/or BEII promoters are preferred to be introduced into the genome of plants, the target promoter DNA molecules to be transcribed (R1, BEI and/or BEII promoter) being under the control of a promoter which controls the expression of said target promoter DNA molecules. The promoter sequences from R1and/or BEI and/or BEII genes necessary for carrying out the present embodiment can be provided by methods known to the skilled person and described in the literature such as in Sambrook and Russell (2001), Molecular Cloning, CSH Press, Cold Spring Harbor, N.Y., U.S.A. The methods may for example include the preparation of a genomic library from the plant in which the activity of R1, BEI and BEII proteins shall be reduced, screening of the library for clones containing the sequence flanking the coding region of the respective gene in 5'-direction by the help of a probe comprising a coding sequence for the R1 or BEI or BEII protein as described above and finally sequencing positive clones by conventional techniques.

Moreover, the skilled person knows that the reduction of activity of one or more R1, BEI and/or BEII proteins can be achieved by means of the expression of non-functional derivatives, in particular trans-dominant mutants of such proteins, and/or by means of the expression of antagonists/inhibitors of such proteins.

Antagonists/inhibitors of such proteins comprise, for instance, antibodies, antibody fragments or molecules having similar binding properties. A cytoplasmatic scFv antibody, for example, was used for modulating the activity of the phytochrome A protein in genetically modified tobacco plants (Owen, Bio/Technology 10 (1992), 790–4; Review: Franken, E., Teuschel, U. and Hain, R., Current Opinion in Biotechnology 8, (1997), 411–416; Whitelam, Trends Plant Sci. 1 (1996), 268–272).

Therefore, a plant cell of the invention is also subject matter of the present invention, wherein said foreign nucleic acid molecule the presence and/or expression of which causes a reduction of R1, BEI and BEII activity in said plant cell is selected from the group consisting of
a) DNA molecules which encode at least one antisense RNA leading to a reduction of the expression of endogenous genes encoding R1 proteins and/or BEI proteins and/or the BEII proteins, preferably encoding R1, BEI and BEII proteins;
b) DNA molecules which, through a co-suppression effect, lead to a reduction of the expression of endogenous genes encoding R1 proteins and/or BEI proteins and/or BEII proteins, preferably encoding R1, BEI and BEII proteins;
c) DNA molecules encoding at least one ribozyme which specifically cleaves transcripts of endogenous genes encoding R1 proteins and/or BEI proteins and/or BEII proteins, preferably encoding R1, BEI and BEII proteins;
d) nucleic acid molecules which have been introduced by means of in-vivo mutagenesis and which lead to a mutation or an insertion of a heterologous sequence in the genes encoding endogenous R1 proteins and/or BEI proteins and/or BEII proteins, preferably encoding R1, BEI and BEII proteins, wherein the mutation or insertion leads to a reduction of the expression of genes encoding R1 proteins and/or BEI proteins and/or BEII proteins, or the synthesis of inactive R1 and/or BEI and/or BEII proteins; and
e) DNA molecules which simultaneously encode at least one antisense RNA and at least one sense RNA, wherein said antisense RNA and said sense RNA form a double-stranded RNA molecule which leads to a reduction of the expression of endogenous genes encoding R1 proteins and/or BEI proteins and/or BEII proteins, preferably encoding R1, BEI and BEII proteins.

In another embodiment, the present invention relates to transgenic plant cells which synthesises a modified starch. The transgenic plant cells of the invention synthesise a modified starch which is modified in its physico-chemical properties, in particular the amylose/amylopectin ratio, the phosphate content, the viscosity behaviour, the size of the starch granules and/or the form of the starch granules in comparison with starch synthesised in wild type plants so that it is more suitable for specific purposes of application.

It was surprisingly found that the composition of the starch is modified in the plant cells of the invention in such a way that it has an amylose content of at least 75% and a reduced phosphate content in comparison with starch from plant cells from corresponding wild type plants, so that said starch is more suitable for specific purposes of application.

A plant cell of the invention which contains modified starch having an amylose content of at least 75% and a reduced phosphate content compared to the starch of corresponding plant cells of wild type plants, the cells not being genetically modified, is also subject matter of the present invention.

In the context of the present invention, the amylose content is determined according to the method by Hovenkamp-Hermelink et al. described below in connection with potato starch (Potato Research 31, (1988), 241–246). This method can also be used for isolated starches of other plant species. The person skilled in the art is familiar with methods for isolating starches.

Within the meaning of the present invention, the term "phosphate content" relates to the content of phosphate bound covalently in form of starch phosphate monoesters.

In the context of the present invention, the expression "reduced phosphate content" means that the overall phosphate content of phosphate covalently bound and/or the phosphate content in the C-6 position of the starch synthesised in the plant cells of the invention is reduced by at least 20%, preferably by at least 50%, more preferably by at least 80% in comparison with starch from plant cells of corresponding wild type plants, the cells not being genetically modified.

Within the meaning of the present invention, the term "phosphate content in the C-6 position" is understood to be the content of phosphate groups which are bound to the carbon atom position "6" of the glucose monomers of the starch. In principle, the positions C2, C3 and C6 of the glucose units may be phosphorylated in the starch in vivo. In connection with the present invention, the phosphate content in the C-6 position (=C6-P content) can be determined through the determination of the glucose-6-phosphate by means of an optic-enzymatic test (Nielsen et al., Plant Physiol. 105, (1994), 111–117) (see below).

In the context of the present invention, the expression "overall phosphate content" of the starch is understood to be the content of phosphate bound covalently in form of starch phosphate monoesters in the C2, C3 and C6 position of the glucose units. According to the invention, the content of phosphorylated non-glucans such as, e.g. phospholipids, is not included in the term "overall phosphate content". Thus, phosphorylated non-glucans must be separated quantitatively before determining the overall phosphate content. The skilled person knows methods for separating the phosphorylated non-glucans (e.g. phospholipids) from the starch. Methods for determining the overall phosphate content are known to the person skilled in the art and are described below.

In a preferred embodiment of the invention, the plant cells of the invention synthesise a starch which has a phosphate content in the C-6 position of the glucose monomers of up to 15 nmol C6-P mg$^{-1}$ starch, in particular of up to 10 nmol C6-P mg$_{-1}$ starch, preferably of up to 7 nmol C6-P mg$^{-1}$ starch, more preferably of up to 4 nmol C6-P mg$^{-1}$ starch.

In another embodiment, the present invention therefore relates to plant cells according to the invention which synthesise a modified starch, wherein the modified starch is characterised in that it has a modified distribution of the side chains. It has been shown that the starch modified in the plant cells of the invention is characterised not only by an increased amylose content and a reduced phosphate content compared to the starch of corresponding wild type plants, but also by a modified distribution of the side chains.

In this embodiment, the term "modified distribution of the side chains" is understood to be an increase in the proportion of short side chains having a DP of 26 to 31 by at least 50%, preferably by at least 100%, more preferably by at least 150% and especially preferred by at least 200% in comparison with the proportion of short side chains having a DP of 26 to 31 of amylopectin from wild type plants. Moreover, the term "modified distribution of the side chains" means an increase of the proportion of short side chains having a DP of 26 to 31, wherein the increase of the proportion of short side chains having a DP of 26 to 31 is not higher than 800%, in particular not higher than 500% compared to the proportion of short side chains having a DP of 26 to 31 of amylopectin from wild type plants. The quantity "DP" means the degree of polymerisation.

The proportion of short side chains is determined by the determination of the proportion in percent that a certain side chain has in the overall proportion of all side chains. The overall proportion of all side chains is determined through the determination of the overall height of the peaks which represent the polymerisation degrees of DP 6 to 40 in the HPLC chromatogram. The proportion in percent that a certain side chain has in the overall proportion of all side chains is determined by the determination of the ratio of the height of the peak representing this side chain in the HPLC chromatogram to the overall height. The program Chromeleon 6.20 by Dionex, USA can, for instance, be used for determining the peak areas.

In another preferred embodiment, the present invention relates to plants cells of the invention which synthesise a modified starch which form a gel after pasting in a 60% (w/v) CaCl$_2$ solution, the gel having an increased gel strength compared to the gel from starch of corresponding wild type plant cells that have not been genetically modified.

Within the meaning of the present invention, the term "increased gel strength" means an increase in the gel strength by at least 1000%, in particular by at least 2500%, preferably by at least 5000% and more preferably by at least 10,000%, by 40,000% at the most or by 30,000% at the most in comparison with the gel strength of starch of corresponding wild type plant cells that have not been genetically modified.

In the context of the present invention, the gel strength is to be determined by means of a texture analyzer under the conditions described below. In this case, the pasting of the starch is achieved in an aqueous 60% (w/v) CaCl$_2$ solution since in a purely aqueous system, it is not possible to achieve pasting of the starch at normal pressure.

In a further preferred embodiment, the present invention relates to plant cells of the invention which, in addition to the aforementioned properties, the starch of which has a modified morphology of the starch granules.

In comparison with high-amylose starches which are known so far, in particular with high-amylose potato starches, the starches of the plant cells of the invention are not only modified in the amylose content, the phosphate content, the distribution of the side chains, the viscosity behaviour and the gel formation behaviour, but also in a modified morphology of the starch granules, which renders these starches more suitable for certain purposes of application.

These starches, in particular the potato starches, could, for instance, be used instead of rice starches since, after mechanical fragmentation, the starches of the invention have an average size of the starch granules which is similar to that of rice starches. Compared to rice starches, the starches of the invention, in particular the potato starches, however have the advantage that they can be sedimented to larger units having the form of a bunch of grapes (cf. Example 2) as small starch granules form bunch-of-grapes-like agglomerations, which may be of advantage in the extraction and processing of the starch and by which the costs may be reduced.

Preferably, the morphology of the starch granules contained in the plant cells of the invention is characterised by an agglomeration of small starch granules having the form of a bunch of grapes.

In a preferred embodiment, the starches contained in the plant cells of the invention are characterised in that the average granule size is reduced compared to the average granule size of corresponding cells of wild type plants which are not genetically modified.

In the context of the present invention, the term "average granule size" means the granule size which can be determined using, for instance, a photo sedimentometer of the type "Lumosed FS1" by Retsch GmbH (see below).

In a further preferred embodiment of the invention, a reduced average granule size is a reduction of the average granule size by at least 20%, preferably by at least 40% and more preferably by at least 60%.

In another preferred embodiment, the starches of the plant cells of the invention are characterised by an average granule size of less than 20 μm, in particular of less than 18 μm, preferably of less than 16 μm and more preferably of 10–15 μm.

In another preferred embodiment of the invention, the starches of the plant cells of the invention are characterised in that the proportion of granules having an average granule size of less than 20 μm is at least 70%, preferably at least 75% and more preferably at least 80%.

After mechanical fragmentation of the starch, which may be carried out as described below, the starches of the plant cells of the invention have a proportion of granules having a granule size of less than 20 μm of at least 80%, preferably of at least 90% and more preferably of at least 95%.

A plurality of techniques is available for introducing DNA into a plant host cell. These techniques comprise the transformation of plant cells with T-DNA using *Agrobacterium tumefaciens* or *Agrobacterium rhizogenes* as a transformation means, the fusion of protoplasts, injection, the electroporation of DNA, the introduction of DNA by means of the biolistic approach, and other possibilities.

The use of the Agrobacteria-mediated transformation of plant cells has been researched into intensively and described sufficiently in EP120516; Hoekema, in: The Binary Plant Vector System, Offsetdrukkerij Kanters B.V., Alblasserdam (1985), Chapter V; Fraley et al., Crit. Rev. Plant Sci. 4, 1–46 and An et al. EMBO J. 4, (1985), 277–287. For the transformation of potato, see, for example, Rocha-Sosa et al. (EMBO J. 8, (1989), 29–33.).

The transformation of monocotyledonous plants by means of *Agrobacterium*-based vectors has also been described (Chan et al., Plant Mol. Biol. 22, (1993), 491–506; Hiei et al., Plant J. 6, (1994) 271–282; Deng et al., Science in China 33, (1990), 28–34; Wilmink et al., Plant Cell Reports 11, (1992), 76–80; May et al., Bio/Technology 13, (1995), 486–492; Conner and Domisse, Int. J. Plant Sci. 153 (1992), 550–555; Ritchie et al., Transgenic Res. 2, (1993), 252–265). An alternative system for the transformation of monocotyledonous plants is the transformation by the biolistic approach (Wan and Lemaux, Plant Physiol. 104, (1994), 37–48; Vasil et al., Bio/Technology 11 (1993), 1553–1558; Ritala et al., Plant Mol. Biol. 24, (1994), 317–325; Spencer et al., Theor. Appl. Genet. 79, (1990), 625–631), protoplast transformation, the electroporation of partially permeabilised cells, and the introduction of DNA by means of glass fibers. The transformation of maize, in particular, has been described repeatedly in the literature (cf., for example, WO 95/06128, EP0513849, EP0465875, EP0292435; Fromm et al., Biotechnology 8, (1990), 833–844; Gordon-Kamm et al., Plant Cell 2, (1990), 603–618; Koziel et al., Biotechnology 11 (1993), 194–200; Moroc et al., Theor. Appl. Genet. 80, (1990), 721–726).

The successful transformation of other cereal species has also been described, for example in the case of barley (Wan and Lemaux, see above; Ritala et al., see above; Krens et al., Nature 296, (1982), 72–74) and wheat (Nehra et al., Plant J. 5, (1994), 285–297). For the expression of the foreign nucleic acid molecule (foreign nucleic acid molecules), in principle, any promoter which is active in plant cells can be used. The promoter can be chosen in such a way that expression in the plants according to the invention is constitutive, or only in a particular tissue, at a particular point in time of plant development, or at a point in time determined by external factors. With respect to the plant, the promoter may be homologous or heterologous. Examples of suitable promoters are the promoter of the cauliflower mosaic virus 35S RNA and the ubiquitin promoter from maize for constitutive expression, the patatin gene promoter B33 (Rocha-Sosa et al., EMBO J. 8 (1989), 23–29), the MCPI promoter of the metallocarboypeptidase inhibitor gene from potato (Hungarian patent application HU9801674) or the GBSSI promoter from potato (international patent application WO 92/11376) for tuber-specific expression in potatoes, or a promoter which ensures expression only in photosynthetically active tissues, for example the ST-LS1 promoter (Stockhaus et al., Proc. Natl. Acad. Sci. USA 84 (1987), 7943–7947; Stockhaus et al., EMBO J. 8 (1989), 2445–2451), the Ca/b promoter (see, for example, U.S. Pat. No. 5,656,496, U.S. Pat. No. 5,639,952, Bansal et al., Proc. Natl. Acad. Sci. USA 89, (1992), 3654–3658) and the rubisco SSU promoter (see, for example, U.S. Pat. No. 5,034,322, U.S. Pat. No. 4,962,028), or the glutelin promoter for an endosperm-specific expression (Leisy et al., Plant Mol. Biol. 14 (1990), 41–50; Zheng et al., Plant J. 4, (1993), 357–366; Yoshihara et al., FEBS Lett. 383, (1996), 213–218), the shrunken-1 promoter (Werr et al., EMBO J. 4, (1985), 1373–1380), the HMG promoter from wheat, the USP promoter, the phaseolin promoter, or promoters of maize zein genes (Pedersen et al., Cell 29, (1982), 1015–1026; Quatroccio et al., Plant Mol. Biol. 15 (1990), 81–93). The expression of the foreign nucleic acid molecule (the foreign nucleic acid molecules) is of particular advantage in organs of the plant that store starch. Such organs are, e.g., the tuber of the potato plant or the kernels or the endosperm of maize, wheat or rice plants. Thus, promoters mediating the expression in these organs are preferred to be used.

However, it is also possible to use promoters which are only activated at a point in time which is determined by external factors (see, for example, WO 93/07279). Promoters of heat shock proteins, which permit simple induction, may be of particular interest in this context. Furthermore, seed-specific promoters such as, for example, the *Vicia faba* USP promoter which ensures seed-specific expression in *Vicia faba* and other plants (Fiedler et al., Plant Mol. Biol. 22, (1993), 669–679; Bäumlein et al., Mol. Gen. Genet. 225, (1991), 459–467) can be used. Other promoters which can be employed are fruit-specific promoters as described, for example, in WO 91/01373. A termination sequence which serves for the correct termination of the transcription and for adding a poly-A tail to the transcript, which is understood to have a function in stabilising the transcripts, may furthermore be present. Such elements have been described in the literature (cf., for example, Gielen et al., EMBO J. 8 (1989), 23–29) and are freely exchangeable.

The plant cells according to the invention may belong to any plant species, i.e. to monocotyledonous or dicotyledonous plants. They are preferably plant cells from agriculturally useful plants, i.e. plants which are grown by man for the purposes of nutrition or for technical, in particular industrial, purposes. The invention preferably relates to fibre-forming (for example flax, hemp, cotton), oil-storing (for example rape, sunflower, soy bean), sugar-storing (for example sugar beet, sugar cane, sugar millet) and protein-storing plants (for example leguminous plants). In a further preferred embodiment, the invention relates to fodder plants, in particular forage grass and pasture grass (alfalfa, clover, etc.) and vegetable plants (for example tomato, lettuce, chicory).

In another preferred embodiment, the invention relates to plant cells from starch-storing plants (for example wheat, barley, oat, rye, potato, maize, rice, pea, cassava), particularly preferred are plant cells from potato.

The plant cells of the invention can be used for regenerating whole plants.

The plants obtainable by regenerating the transgenic plant cells of the invention are also subject matter of the present invention.

Furthermore, plants which contain the transgenic plant cells of the invention are also subject matter of the invention.

The transgenic plants may, in principle be plants belonging to any plant species, i.e. both monocotyledonous and dicotyledonous plants. They are preferably useful plants, i.e. plants which are grown by man for the purposes of nutrition or for technical, in particular industrial, purposes. The invention preferably relates to plant cells of fibre-forming (for example flax, hemp, cotton), oil-storing (for example rape, sunflower, soy bean), sugar-storing (for example sugar beet, sugar cane, sugar millet) and protein-storing plants (for example leguminous plants). In a further preferred embodiment, the invention relates to fodder plants, in particular forage grass and pasture grass (alfalfa, clover, etc.) and vegetable plants (for example tomato, lettuce, chicory).

In another preferred embodiment, the invention relates to starch-storing plants (for example wheat, barley, oat, rye, potato, maize, rice, pea, cassava), particularly preferred are potato plants.

The present invention also relates to a method for the production of a transgenic plant cell which synthesises a modified starch, wherein a plant cell is genetically modified by introducing one or more foreign nucleic acid molecules, the presence and/or expression of which leads to a reduction of the activity of R1, BEI and BEII proteins compared to corresponding plants cells of wild type plants, the cells not being genetically modified.

In a preferred embodiment of the method of the invention, the modified starch is characterised in that it has an amylose content of at least 75% and a reduced phosphate content in comparison with starch from corresponding wild type plants which are not genetically modified.

The present invention also relates to a method for producing a transgenic plant which synthesises modified starch, wherein
a) a plant cell is genetically modified by introducing one or more foreign nucleic acid molecules the presence and/or expression of which leads to a reduction of the activity of R1, BEI and BEII proteins compared to corresponding plant cells of wild type plants, the cells not being genetically modified;
b) a plant is regenerated from the cell produced according to a); and
c) optionally further plants are produced from the plant produced according to step b).

In a preferred embodiment of the method of the invention, the modified starch is characterised in that it has an amylose content of at least 75% and a reduced phosphate content compared to the starch from corresponding wild type plants which are not genetically modified.

In another embodiment of the method of the invention, the modified starches moreover have a modified distribution of the side chains and/or a modified morphology of the starch granules and/or a reduced average size of the starch granules and/or form a gel after pasting in an aqueous 60% (w/v) $CaCl_2$ solution, the gel having an increased gel strength in comparison with a gel of starch from corresponding wild type plants which are not genetically modified. The same as has already been said above in connection with the plant cells of the invention also applies to the genetic modification introduced according to step a). Regeneration, of plants according to step b) can be made using methods known to the person skilled in the art.

Further plants of the methods of the invention can be produced according to step c) by means of vegetative propagation (for example using cuttings, tubers or by means of callus culture and regeneration of whole plants) or by generative propagation. Generative propagation is preferably done under controlled conditions, i.e. selected plants having specific properties are crossed with each other and propagated. The person skilled in the art obviously knows that, for producing the plant cells and plants of the invention, also transgenic plants can be used in which the activity of one or two of the aforementioned proteins has already been reduced and which, according to the method of the invention, only have to be genetically modified in such a way that the activity of the second or third protein is also reduced.

In addition, the skilled person knows that the aforementioned super-transformation is not necessarily carried out with primary transformants but preferably with pre-selected stable transgenic plants which advantageously have already been tested for, e.g. fertility, stable expression of the foreign gene, hemizygosity and heterozygosity, etc. in corresponding experiments.

The present invention also relates to the plants obtainable by the methods of the invention.

The present invention also relates to propagation material of plants of the invention containing plant cells of the invention as well as of the plants produced according to the methods of the invention. Within the meaning of the present invention, the term "propagation material" comprises parts of the plant which are suitable for producing progeny by the vegetative or generative route. Examples which are suitable for vegetative propagation are cuttings, callus cultures, rhizomes or tubers. Other propagation material encompasses, for example, fruits, seeds, seedlings, protoplasts, cell cultures and the like. The propagation material is preferably seeds.

Furthermore, the present invention relates to the use of one or more foreign nucleic acid molecules encoding proteins having the enzymatic activity of R1, BEI and BEII proteins and to the use of fragments of said foreign nucleic acid molecules for producing plant cells or plants of the invention synthesising a modified starch.

In another embodiment of the invention, the plant cells of the invention synthesise a modified starch due to the use according to the invention of one or more foreign nucleic acid molecules, the modified starch being characterised in that it has an amylose content of at least 75% and/or a reduced phosphate content compared to the starch of corresponding wild type plants which have not been genetically modified and/or a modified distribution of the side chains and/or a modified morphology of the starch granules and/or a reduced average size of the starch granules and/or a modified starch which forms a gel after pasting in an aqueous 60% (w/v) $CaCl_2$ solution, the gel having an increased gel strength in comparison with a gel of starch from corresponding wild type plant cells which are not genetically modified.

In another embodiment, the present invention relates to the use of one or more foreign nucleic acid molecules for producing plants of the invention, wherein the foreign nucleic acid molecule is a molecule, or the foreign nucleic acid molecules are several molecules selected from the group consisting of
a) DNA molecules which encode at least one antisense RNA leading to a reduction of the expression of endogenous genes encoding the R1 proteins and/or BEI proteins and/or the BEII proteins, preferably encoding R1, BEI and BEII proteins;
b) DNA molecules which, through a co-suppression effect, lead to the reduction of the expression of endogenous genes encoding R1 proteins and/or BEI proteins and/or BEII proteins, preferably encoding R1, BEI and BEII proteins;
c) DNA molecules encoding at least one ribozyme which specifically cleaves transcripts of endogenous genes encoding R1 proteins and/or BEI proteins and/or BEII proteins, preferably encoding R1, BEI and BEII proteins;
d) nucleic acid molecules which have been introduced by means of in-vivo mutagenesis and which lead to a mutation or an insertion of a heterologous sequence in the genes encoding endogenous R1 proteins and/or BEI proteins and/or BEII proteins, preferably encoding R1, BEI and BEII proteins, wherein the mutation or insertion leads to a reduction of the expression of the genes encoding R1 proteins and/or BEI proteins and/or BEII proteins, or the synthesis of inactive R1 and/or BEI and/or BEII proteins; and
e) DNA molecules which simultaneously encode at least one antisense RNA and at least one sense RNA, wherein said antisense RNA and said sense RNA form a double-stranded RNA molecule which leads to a reduction of the expression of endogenous genes encoding R1 proteins and/or BEI proteins and/or BEII proteins, preferably encoding R1, BEI and BEII proteins.

As has already been explained before, the foreign nucleic acid molecules can be introduced simultaneously or consecutively, i.e. one after the other, into the genome of the plant cell. The simultaneous introduction of the foreign nucleic acid molecules saves time and costs, i.e. the co-transformation in which, preferably in one transformation experiment according to the aforementioned methods of the invention, foreign nucleic acid molecules are introduced into the plant cell, the presence and optionally the expression of which lead to the reduction of the activity of one or more R1 proteins occurring endogenously in the plant cell and to the reduction of the activity of one or more BEI proteins occurring endogenously in the plant cell and to the reduction of the activity of one or more BEII proteins occurring endogenously in the plant cell in comparison with corresponding plant cells of wild type plants, the cells not being genetically modified.

Thus, the present invention also relates to compositions containing at least one of the foreign nucleic acid molecules defined according to the invention, these foreign nucleic acid molecules being suitable for producing the transgenic plant cells and/or the transgenic plants of the invention. Preferably, the presence and/or expression of these foreign nucleic acid molecules in plant cells leads to the reduction of the activity of R1 and BEI and BEII proteins compared to corresponding plant cells of wild type plants, the cells not being genetically modified.

In this case, in the composition of the invention, the nucleic acid molecules the presence and/or expression of which in the plant cell and/or the plant leads to the reduction of the activity of R1 and BEI and BEII proteins compared to corresponding plant cells of wild type plants, the cells not being genetically modified, can be contained either separately or together in one recombinant nucleic acid molecule. In the former case, the composition of the invention can, for instance, contain two or more recombinant nucleic acid molecules and/or vectors the joint presence of which in the plant cell leads to said phenotype. In the latter case, a recombinant nucleic acid molecule contains the genetic information leading to the reduction of the activity of R1 and BEI and BEII proteins compared to corresponding plant cells of wild type plants, the cells not being genetically modified.

In such a recombinant molecule, for instance, the above-described foreign nucleic acid molecules the presence and/or expression of which in a plant cell leads to the reduction of the activity of R1 and BEI and BEII proteins compared to corresponding plant cells of wild type plants, the cells not being genetically modified, can be present as one chimeric gene or as separate genes. Examples of such double or multiple constructs have been described numerously in the literature.

The aforementioned recombinant nucleic acid molecules can be present in any host cell.

In another embodiment, the present invention therefore also relates to a host cell, in particular a plant cell, containing a composition of the invention.

The plant cells and plants of the invention synthesise a starch, in particular in their starch-storing organs, which is modified in its physico-chemical properties, in particular the phosphate content and/or the amylose content, preferably the phosphate content and the amylose content, and/or the distribution of the side chains and/or the viscosity behaviour and/or the morphology of the starch granules and/or the average size of the starch granules in comparison with starch synthesised in wild type plants.

Thus, starch which is obtainable from the plant cells, plants and/or propagation material of the invention is also subject matter of the invention.

In a preferred embodiment, the starch of the invention is characterised in that it has an amylose content of at least 75% and a reduced phosphate content in comparison with starch from corresponding wild type plants which are not genetically modified.

The meaning of the term "increased gel strength" has already been defined in connection with the description of the plant cells of the invention.

In comparison with high-amylose starches which are known so far, in particular with high-amylose potato starches, the starches of the invention are not only modified in the amylose content, the phosphate content, the distribution of the side chains, the viscosity behaviour and the gel formation behaviour, but also in a modified morphology of the starch granules, which renders these starches more suitable for certain purposes of application.

The starches of the invention, in particular the potato starches, could, for instance, be used instead of rice starches since, after mechanical fragmentation, the starches of the invention have an average size of the starch granules which is similar to that of rice starches. Compared to rice starches, the starches of the invention, in particular the potato starches, however have the advantage that they can be sedimented to larger units having the form of a bunch of grapes (cf. Example 2) as small starch granules form bunch-of-grapes-like agglomerations, which may be of advantage in the extraction and processing of the starch and by which the costs may be reduced.

Preferably, morphology of the starch granules of the starch of the invention is characterised by an agglomeration of small starch granules having the form of a bunch of grapes.

In another embodiment, the starches of the invention are characterised in that the average granule size is reduced compared to the average granule size of corresponding wild type plants which are not genetically modified.

In the context of the present invention, the term "average granule size" means the granule size which can be determined using, for instance, a photo sedimentometer of the type "Lumosed FS1" by Retsch GmbH (see below).

In another embodiment of the invention, a reduced average granule size is a reduction of the average granule size by at least 20%, preferably by at least 40% and more preferably by at least 60%.

In another embodiment, the starches of the invention are characterised by an average granule size of less than 20 µm, in particular of less than 18 µm, preferably of less than 16 µm and more preferably of 10–15µm.

In another embodiment of the invention, the starches of the invention are characterised in that the proportion of granules having an average granule size of less than 20 µm is at least 70%, preferably at least 75% and more preferably at least 80%.

After mechanical fragmentation of the starch, which may be carried out as described below, the starches of the invention have a proportion of granules having a granule size of less than 20 µm of at least 80%, preferably of at least 90% and more preferably of at least 95%.

In a particularly preferred embodiment, the starch of the invention is a potato starch. Moreover, the present invention relates to a method for producing the starches of the invention comprising the step of extracting the starch from a plant (cell) of the invention and/or from starch-storing parts of such a plant.

Preferably, such a method also comprises the step of harvesting the cultivated plants and/or starch-storing parts of said plants prior to extracting the starch and, particularly preferably, the step of cultivating the plants of the invention prior to the harvesting.

The person skilled in the art knows methods for extracting the starch from plants or from starch-storing parts of plants. Furthermore, methods for extracting the starch from various starch-storing plants have been described, e.g. in "Starch: Chemistry and Technology (editors.: Whistler, BeMiller and Paschall (1994), $2^{nd}$ edition, Academic Press Inc. London Ltd.; ISBN 0-12-746270-8; cf., e.g. chapter XII, page 412–468: maize and sorghum starches: production; by Watson; Chapter XIII, page 469–479: tapioca, arrowroot and sago starches: production; by Corbishley and Miller; Chapter XIV, page 479–490: potato starch: production and uses; by Mitch; Chapter XV, page 491 to 506: wheat starch: production, modification and uses; by Knight and Oson; and Chapter XVI, page 507 to 528: rice starch: production and uses; by Rohmer and Klem; maize starch: Eckhoff et al., Cereal Chem. 73 (1996) 54–57), the extraction of maize starch on an industrial scale is generally achieved by wet milling. Apparatuses usually used in processes for extracting starch from plant materials are separators, decanters, hydrocyclones, spray dryers and fluidized-bed dryers.

Moreover, starch which is obtainable using the aforementioned method of the invention is also subject matter of the invention.

The starches according to the invention can be modified afterwards by processes known to the skilled person and are suitable, in their unmodified or modified forms, known to the skilled person and are suitable, in their unmodified or modified forms, for a variety of applications in the food or non-food sector.

DETAILED DESCRIPTION OF THE INVENTION

Figure 1:
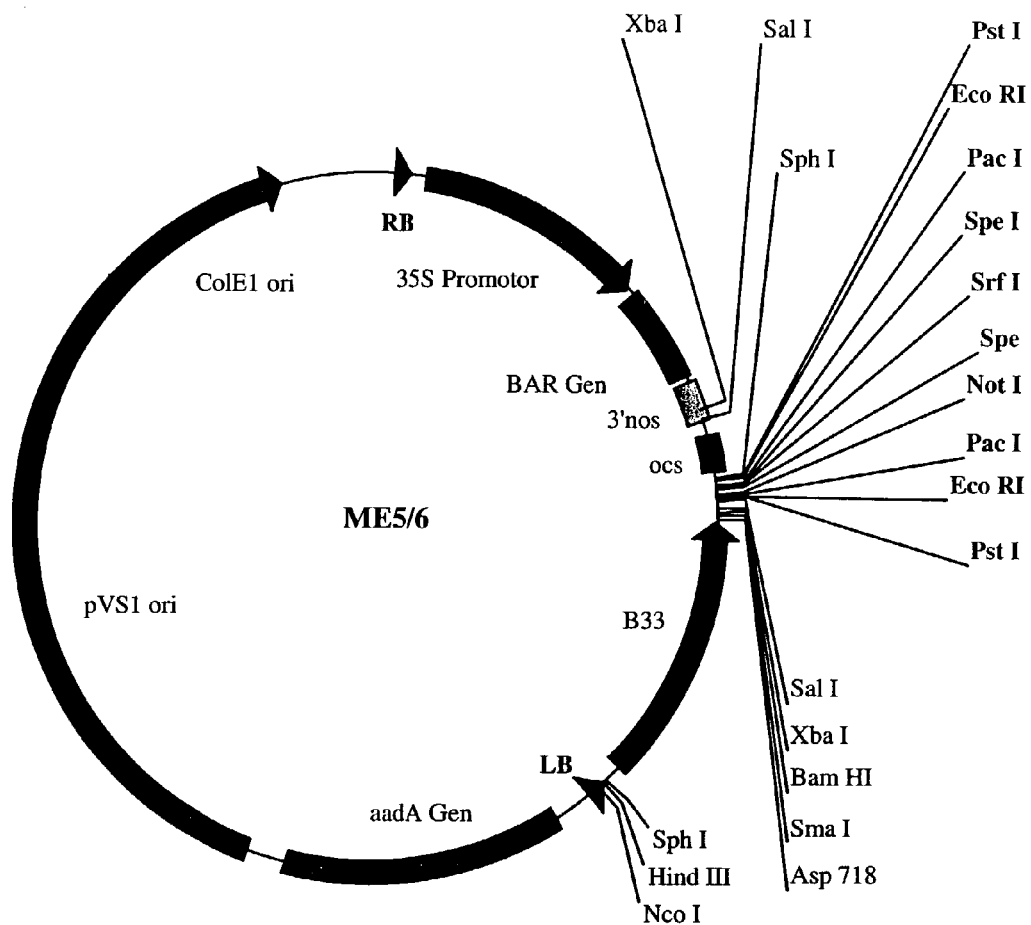
FIG. 1: Schematic representation of the expression vector ME 5/6 as described further below.

The Following Methods were Used in the Examples

Analysis of the Starch a) Determination of the Amylose/Amylopectin Ratio

Starch was isolated from potato plants according to standard techniques and the ratio of amylose to amylopectin was determined using the method described by Hovenkamp-Hermelink et al. (Potato Research 31, (1988), 241–246).

b) Determination of the Phosphate Content

The positions C2, C3 and C6 of the glucose units may be phosphorylated in the starch. For determining the C6-P content of the starch, 50 mg starch are hydrolysed in 500 μl 0.7 M HCl for 4 hours at 95° C. Then, the mixtures are centrifuged for 10 min at 15,500 g and the supernatants are taken. 7 μl of the supernatants are mixed with 193 μl imidazole buffer (100 mM imidazole, pH 7.4; 5 mM $MgCl_2$, 1 mM EDTA and 0.4 mM NAD). The measuring was carried out in the photometer at 340 nm. After establishing a basic absorption, the enzyme reaction was started by adding 2 u glucose-6 phosphate dehydrogenase (from Leuconostoc mesenteroides, Boehringer Mannheim). The change in the absorption is directly proportional to the concentration of the G-6-P content of the starch.

The overall phosphate content was determined according to the method by Ames (Methods in Enzymology VIII, (1966), 115–118).

30 μl ethanolic magnesium nitrate solution are added to about 50 mg starch and ashed for three hours at 500° C. in a muffle furnace. 300 μl 0.5 M hydrochloric acid are added to the residue and incubated for 30 min at 60° C. Then, an aliquot is filled to 300 μl 0.5 M hydrochloric acid, added to a mixture of 100 μl 10% ascorbic acid and 600 μl 0.42% ammonium molybdate in 2 M sulphuric acid and incubated for 20 min at 45° C.

Then, a photometric measurement is conducted at 820 nm, using a phosphate calibration series as a standard.

c) Determination of the Gel Strength (Texture Analyser)

2 g starch (TS) are dissolved in 25 ml of an aqueous 60% (w/v) $CaCl_2$ solution and pasting is achieved in an RVA apparatus (temperature program: cf. item d) "Determination of the viscosity properties by means of a Rapid Visco Analyser (RVA)") and then it is stored in a closed container for 24 hours at room temperature. The samples are fixed under a probe (cylindrical stamp with a planar surface) of a texture analyser TA-XT2 by Stable Micro Systems (Surrey, UK) and the gel strength is determined using the following parameters:

| test speed | 0.5 mm/s |
|---|---|
| depth of penetration | 7 mm |
| contact area | 113 mm$^2$ |
| pressure | 2 g | d) Determination of the Viscosity Properties by Means of a Rapid Visco Analyser (RVA)

2 g starch (TS) are added to 25 ml $H_2O$ and used for the analysis in a Rapid Visco Analyser (Newport Scientific Pty Ltd., Investment Support Group, Warriewod NSW 2102, Australia). The apparatus is used according to the manufacturer's instructions. For determining the viscosity of the aqueous solution of the starch, the starch suspension is first heated to 50° C. for 1 min, then it is heated from 50° C. to 95° C. at a speed of 12° C. per minute. Subsequently, the temperature is maintained at 95° C. for 2.5 min. Then, the solution is cooled down from 95° C. to 50° C. at a speed of 12° C. per minute. The viscosity is determined over the whole time.

e) Determination of Glucose, Fructose and Sucrose

The content of glucose, fructose and sucrose is determined according to the method described by Stitt et al. (Methods in Enzymology 174, (1989), 518–552).

f) Analysis of the Distribution of the Side Chains of the Amylopectin by Means of Ion Exchange Chromatography For separating amylose from amylopectin, 200 mg starch are dissolved in 50 ml-reaction vessels with 12 ml 90% (v/v) DMSO in $H_2O$. After adding 3 volumes ethanol, the precipitate is separated by a 10 min-centrifugation at about 1800 g at room temperature (RT). The pellet is then washed with 30 ml ethanol, dried and dissolved in 40 ml 1% (w/v) NaCl solution at 75° C. After cooling down the solution to 30° C., about 90 mg thymol are added slowly and this solution is incubated for at least 60 h at 30° C. Then, the solution is centrifuged for 30 min at 2000 g (RT). 3 volumes ethanol are then added to the supernatant and the precipitating amylopectin is separated by means of 5 min-centrifugation at 2000 g (RT). The pellet (amylopectin) is then washed with ethanol and dried using acetone. By adding DMSO to the pellet, a 1%-solution is prepared 200 µl of which are added to 345 µl water, 10 µl 0.5 M sodium acetate (pH 3.5) and 5 µl isoamylase (dilution of 1:10; Megazyme) and incubated for about 16 h at 37° C. An aqueous 1:5 dilution of this digestion is then filtered with an 0.2 µm-filter and 100 µl of the filtrate are analysed by means of ion exchange chromatography (HPAEC-PAD, Dionex). The separation is carried out with a PA-100 column (with a corresponding pre-column), the detection is carried out amperometrically. The elution conditions are as follows:

| t (min) | solution A (%) | solution B (%) |
|---|---|---|
| 5 | 0 | 100 |
| 35 | 30 | 70 |
| 45 | 32 | 68 |
| 60 | 100 | 0 |
| 70 | 100 | 0 |
| 72 | 0 | 100 |
| 80 | 0 | 100 |
| stop | | | solution A—0.15 M NaOH
solution B—1 M sodium acetate in 0.15 M NaOH

The relative proportion of short side chains in the overall proportion of all side chains is determined by determining the proportion in percent that a certain side chain has in the overall proportion of all side chains. The overall proportion of all side chains determined through the determination of the overall height of the peaks which represent the polymerisation degrees of DP 6 to 40 in the HPLC chromatogram. The proportion in percent that a certain side chain has in the overall proportion of all side chains is determined by the determination of the ratio of the height of the peak representing this side chain in the HPLC chromatogram to the overall height of all peaks having a DP of 6 to 40. The program Chomeleon 6.20 by Dionex, USA was used for determining the peak heights. The parameters of the evaluation software that were to be adjusted were as follows:

| retention time (min) | parameter name | parameter value | channels |
|---|---|---|---|
| 0.000 | Inhibit Integration | on | All channels |
| 20.000 | Lock Baseline | on | All channels |
| 20.600 | Inhibit Integration | off | All channels |
| 20.600 | Minimum Height | 0.001 (Signal) | All channels |
| 45.000 | Inhibit Integration | on | All channels | g) Determination of the Granule Size

Starch was extracted from the potato tubers according to standard methods and washed several times with water in a 10 l-bucket (ratio height of the bucket/diameter of the bucket=approx. 1.1). For obtaining the starch samples which were finally subjected to the determination of the granule size, the starches were left to stand for about 4 h after washing to achieve as complete a sedimentation of the starches as possible.

The granule size was then determined by means of a photo sedimentometer of the type "Lumosed FS1" by Retsch GmbH, Germany using the software V.2.3.

The software adjustments were as follows:

| data of the substance: | calibration no. | 0 |
|---|---|---|
| | density [kg/m$^3$] | 1500 |
| sedimentation fluid: | type | water |
| | viscosity [Pa s] | 0.001 |
| | density [kg/m$^3$] | 1000 |
| | addition | — |
| | measurement data | 5 min |
| | sieve diameter [µm] | 250 |
| | passage [%] | 100 |
| | measurement range | 4.34–117.39 µm |
| | calibration | N |
| | temperature | 20° C. |

The distribution of the granule size was determined in an aqueous solution and according to the manufacturer's instructions and based on the literature of e.g. H. Pitsch, Korngrößenbestimmung; LABO-1988/3 Fachzeitschrift für Labortechnik, Darmstadt.

h) Mechanical Fragmentation of the Strach

About 0.5 g of each starch were placed in a coffee mill (manufacturer: Mellert, type: M85, Germany) and ground six times for 30 s each. Between two intervals, the grinding was interrupted for 20 s each. The distribution of the granule size was determined as described in item g).

i) Water Binding Capacity

For determining the water binding capacity (WBC), the supernatant was weighed after separating the soluble portion by centrifugation of the starch swollen at 70° C. The water binding capacity (WBC) of the starch was set in relation to the weighed portion of the starch corrected by the soluble mass.

WBC (g/g)=(residue−(weighed portion−soluble portion))/(weighed portion−soluble portion).

The expression vector ME5/6 (cf. FIG. 1) was used in the Examples:

Preparation of the Expression Vector ME5/6 pGSV71 is a derivative of the plasmid pGSV7 which is derived from the intermediary vector pGSV1. pGSV1 is a derivative of pGSC1700 the construction of which has been described by Cornelissen and Vanderwiele (Nucleic Acids Research 17, (1989), 19–25). pGSV1 was obtained from pGSC1700 by deletion of the carbenicillin resistance gene as well as deletion of the T-DNA sequences of the TL-DNA region of the plasmid pTiB6S3.

pGSV7 contains the replication origin of the plasmid pBR322 (Bolivar et al., Gene 2, (1977), 95–113) as well as the replication origin of the *Pseudomonas* plasmid pSV1 (Itoh et al., Plasmid 11, (1984), 206). pGSV7 additionally contains the selectable marker gene aadA from the transposon Tn1331 from *Klebsiella pneumoniae* which confers resistance to the antibiotics spectinomycin and streptomycin (Tolmasky, Plasmid 24 (3), (1990), 218–226; Tolmasky and Crosa, Plasmid 29 (1), (1993), 31–40).

The plasmid pGSV71 was obtained by cloning a chimeric bar gene between the border regions of pGSV7. The chimeric bar gene contains the promoter sequence of the cauliflower mosaic virus for initiating the transcription (Odell et al., Nature 313, (1985), 180), the bar gene from *Streptomyces hygroscopicus* (Thompson et al., EMBO J. 6, (1987), 2519–2523) and the 3'-non-translated region of the nopaline synthase gene of the T-DNA of pTiT37, for terminating the transcription and polyadenylation. The bar gene confers resistance to the herbicide glufosinate ammonium.

In position 198–222, the T-DNA contains the right border sequence of the TL-DNA of the plasmid pTiB6S3 (Gielen et al., EMBO J. 3, (1984), 835–846). There is a polylinker sequence between the nucleotide 223–249. The nucleotides 250–1634 contain the P35S3 promoter region of the cauliflower mosaic virus (Odell et al., cf. above). The coding sequence of the phosphinothricine resistance gene (bar) from *Streptomyces hygroscopicus* (Thompson et al., 1987, cf. above) is contained between the nucleotides 1635–2186. The two terminal codons at the 5' end of the bar wild type gene were replaced by the codons ATG and GAC. There is a polylinker sequence between the nucleotides 2187–2205. The 260 bp-TaqI fragment of the non-translated 3' end of the nopaline synthase gene (3'nos) from the T-DNA of the plasmid pTiT37 (Depicker et al., J. Mol. Appl. Genet. 1, (1982), 561–573 is located between the nucleotides 2206 and 2465. The nucleotides 2466–2519 contain a polylinker sequence. The left border sequence of the TL-DNA from pTiB6S3 (Gielen et al., EMBO J. 3, (1984), 835–846) is located between the nucleotides 2520–2544.

The vector pGSV71 was then cleaved with the enzyme PstI and blunted. The promoter B33 and the ocs cassette were cleaved from the vector pB33-Kan as an EcoRI-HindIII fragment, blunted and inserted into the vector pGSV71 which had been cleaved with PstI and blunted. The vector obtained served as a starting vector for the construction of ME5/6. An oligonucleotide containing the cleavage sites EcoRI, PacI, SpeI, SrI, SpeI, NotI, PacI and EcoRI was inserted into the PstI cleavage site between the B33 promoter and the ocs element of the vector ME4/6 by duplicating the PstI cleavage site. The expression vector obtained was called ME5/6.

Description of the Vector pSK-Pac pSK-Pac is a derivative of pSK Bluescript (Stratagene, USA) into which PacI cleavage sites flanking the multiple cloning site (MCS) were inserted.

The following Examples illustrate the invention:

EXAMPLE 1

Production of Transgenic Potato Plants having a Reduced Gene Expression of an R1, BEI and BEII Gene For producing transgenic plants having a reduced activity of a BEI, R1 and BEII protein, first transgenic plants were generated in which the BE1 activity and the amount of protein R1 were reduced. For this purpose, both the T-DNA of the plasmid pB33-aR1-Hyg and the T-DNA of the plasmid pB33-a-BE1-Kan were transferred simultaneously into potato plants using Agrobacteria as described by Rocha-Sosa et al. (EMBO J. 8, (1989), 23–29).

For constructing the plasmid pB33-aR1-Hyg and the plasmid pB33-aBE1-Kan, first the expression vectors pB33-Kan and pb33-Hyg, respectively, were constructed. For this purpose, the promoter of the patatin gene B33 from *Solanum tuberosum* (Rocha-Sosa et al., 1989, cf. above) was ligated as DraI fragment (nucleotides −1512 to +14) into the vector pUC19 (GenBank Acc. No. M77789) which had been cleaved with SstI, the ends of said vector having been blunted by means of the T4-DNA polymerase. In this way, the plasmid pUC19-B33 was obtained. The B33 promoter was cleaved from this plasmid with EcoRI and SmaI and ligated into the vector pBinAR which had been cleaved correspondingly. In this way, the plant expression vector pB33-Kan was obtained. The plasmid pBinAR is a derivative of the vector plasmid pBin19 (Bevan, Nucl. Acids Research 12, (1984), 8711–8721) and was constructed by Höfgen and Willmitzer (Plant Sci. 66, (1990), 221–230). Starting from plasmid pB33-Kan, the EcoRI-HindIII fragment comprising the B33 promoter, a portion of the polylinker and the ocs terminator from pB33-Kan were cleaved and ligated into the vector pBIB-Hyg (Becker, Nucleic Acids Res. 18 (1), (1990), 203) which had been cleaved correspondingly. As a result, pB33-Hyg was obtained.

Then, an approximately 2000 bp-Asp718 fragment of the plasmid pRL1 which contains the nucleotide sequence of about +2850 to about +4850 of the R1 cDNA from *Solanum tuberosum* (Lorberth, Charakterisierung von RL1: ein neues Enzym des Stärkemetabolismus. Dissertation Freie Universität Berlin) in antisense orientation into the Asp718 cleavage site of the plasmid described before. The resulting plasmid was called pB33-aR1-Hyg. For constructing the plasmid pB33-aBE1-Kan, analogously to the aforementioned strategy, the promoter region of the patatin-class-I gene B33 from *Solanum tuberosum*—a SmaI/HindIII fragment which has a length of about 3100 bp and contains a partial cDNA for the BE1 enzyme from potato (Kossmann, Klonierung und funktionelle Analyse von Genen codierend für am Kohlenhydratstoffwechsel der Kartoffel beteiligte Proteine, Dissertation Technische Universität Berlin, (1992))—was first blunted and inserted into the SmaI cleavage site of the vector pBinAR-Hyg (cf. above) in antisense orientation with regard to the B33 promoter.

After the transformation, different lines of transgenic potato plants could be identified by means of Western blot analysis, the tubers of said potatoes having a content of the R1 protein which was reduced significantly. Further analyses showed that isolated starch of the line 36 had the highest amylose content of all transformants examined independently of each other.

Plants of said line were then transformed with the plasmid pGSV71-aBE2-basta as described by Rocha-Sosa et al. (EMBO J. 8 (1989), 23–29).

Plasmid pGSV71-aBE2-basta was constructed by screening according to standard procedures a tuber-specific potato cDNA library with a DNA fragment which had been amplified by RT-PCR (primer 1 (SEQ ID No. 1): 5'-gggggtgttg-gctttgacta and primer 2 (SEQ ID No. 2) 5'-ccttctcctcctaatc-cca; Stratagene ProSTAR™ HF Single-Tube RT-PCR system) with total-RNA from tubers as template. In this way, a DNA fragment which has a size of about 1250 bp (cf. SEQ ID No. 3) and which was then subcloned as a EcoRV-SmaI fragment into the EcoRV cleavage site of the cloning vector pSK-Pac (cf. above) and finally ligated as PacI fragment into the expression vector ME5/6 (FIG. 1) in antisense orientation. As a result, the plasmid pGSV71-aBE2-basta was obtained.

From plants which were obtained by the transformation with the plasmid pGSV71-aBE2-basta and which showed a reduced R1, BEI and BEII gene expression, said plants being called 203MH plants, tissue samples of tubers of the independent transformants were taken and their amylose content was determined (cf. methods). The starches of the independent lines the tubers of which had the highest amylose content were used for further analysing the starch properties (cf. Example 2).

EXAMPLE 2

Analysis of the Starch of Plants Having a Reduced R1, BEI and BEII Gene Expression The starch of different independent lines of the transformation 203 MH described in Example 1 was isolated from potato tubers. Then, the physico-chemical properties of this starch were analysed. The results of the characterisation of the modified starches are shown in Table 1 (Tab. 1) for an exemplary selection of certain plant lines.

TABLE 1

| no. | genotype | phosphate in C6 (%) | amylose (%) | RVA max (%) | RVA min (%) | RVA fin (%) | RVA set (%) | RVA T (%) | gel strength, 60% (w/v) CaCl$_2$ (%) |
|---|---|---|---|---|---|---|---|---|---|
| 1 | Desiree (wild type) | 100 | 22 | 100 | 100 | 100 | 100 | 100 | 100 |
| 3 | 203MH010 | 25 | 92 | | no pasting in H$_2$O | | | | approx. 17,000 |
| 5 | 203MH055 | 33 | 80 | | | | | | not measured |
| 6 | 203MH080 | 31 | 91 | | | | | | approx. 10,600 |

Legend:
R1 = R1 enzyme, BEI = branching enzyme I, BEII = branching enzyme II, as = antisense
RVA = Rapid Visco Analyser,
max = maximum viscosity,
min = minimum viscosity
fin = viscosity at the end of the measurement,
set = set back = difference of min und fin
T = pasting temperature
The values in % are related to the wild type (=100%) except for the amylose content.

The distribution of the side chains of the amylopectin was analysed as described above. The following Table (Tab. 2) contains an overview of the proportions of the individual peak heights of the HPAEC chromatograms within the overall peak height of wild type plants (Desiree), of 072VL036 plants (potato plants having a reduced gene expression of the R1 and BEI gene) and of selected lines of the transformations 203MH (cf. Example 1: potato plants having a reduced gene expression of the R1, BEI and BEII gene):

TABLE 2

| no. of glucose units | proportion of the individual peak heights within the overall peak height of every potato line in % | | | | |
|---|---|---|---|---|---|
| | Desi Mix | 072VL036 | 203MH10 | 203MH61 | 203MH80 |
| dp6 | 2.48 | 1.2 | 2.6 | 1.7 | 2.7 |
| dp7 | 1.90 | 1.2 | 1.6 | 1.1 | 1.5 |
| dp8 | 1.46 | 1.4 | 1.0 | 0.8 | 1.2 |
| dp9 | 2.48 | 2.2 | 1.3 | 1.1 | 1.5 |
| dp10 | 4.38 | 3.5 | 2.1 | 1.9 | 2.1 |
| dp11 | 6.28 | 4.8 | 3.1 | 2.8 | 3.0 |
| dp12 | 7.30 | 5.6 | 3.6 | 3.6 | 3.3 |
| dp13 | 7.88 | 6.1 | 3.6 | 3.9 | 3.3 |
| dp14 | 7.88 | 6.3 | 3.9 | 4.4 | 3.6 |
| dp15 | 7.30 | 6.3 | 4.2 | 4.4 | 3.3 |
| dp16 | 6.72 | 6.1 | 4.2 | 4.7 | 3.3 |
| dp17 | 5.84 | 5.9 | 4.2 | 4.7 | 3.3 |
| dp18 | 5.26 | 5.7 | 4.4 | 4.7 | 3.3 |
| dp19 | 4.82 | 5.5 | 4.4 | 4.7 | 3.3 |
| dp20 | 4.38 | 5.1 | 4.4 | 4.7 | 3.3 |
| dp21 | 3.94 | 4.7 | 4.4 | 4.7 | 3.6 |
| dp22 | 3.50 | 4.2 | 4.2 | 4.7 | 3.6 |
| dp23 | 3.07 | 3.8 | 4.2 | 4.4 | 3.9 |
| dp24 | 2.48 | 3.4 | 4.4 | 4.4 | 4.2 |
| dp25 | 2.19 | 3.1 | 4.2 | 4.4 | 4.2 |
| dp26 | 1.90 | 2.7 | 4.2 | 4.2 | 4.5 |
| dp27 | 1.75 | 2.4 | 3.9 | 4.2 | 4.5 |
| dp28 | 1.31 | 2.0 | 3.6 | 3.6 | 4.5 |
| dp29 | 1.02 | 1.6 | 3.4 | 3.3 | 4.2 |
| dp30 | 0.88 | 1.3 | 2.9 | 2.8 | 3.9 |
| dp31 | 0.58 | 1.1 | 2.6 | 2.5 | 3.3 |
| dp32 | 0.44 | 0.8 | 2.1 | 1.9 | 2.7 |
| dp33 | 0.29 | 0.7 | 1.8 | 1.7 | 2.4 |
| dp34 | 0.29 | 0.5 | 1.8 | 1.4 | 2.4 |
| dp35 | 0.00 | 0.4 | 1.6 | 1.1 | 1.8 |
| dp36 | 0.00 | 0.3 | 1.0 | 0.8 | 1.5 |
| dp37 | 0.00 | 0.2 | 0.8 | 0.6 | 0.9 |
| dp38 | 0.00 | 0.2 | 0.5 | 0.0 | 0.9 |
| dp39 | 0.00 | 0.0 | 0.0 | 0.0 | 0.0 |
| dp40 | 0.00 | 0.0 | 0.0 | 0.0 | 0.0 |
| Total | 100.00 | 100.0 | 100.0 | 100.0 | 100.0 |

If the proportion of peak heights of the individual chain lengths (indicated in DP) in the overall peak height is compared, a considerable shift towards side chains having a DP>26 can be seen with regard to the distribution of the side chains of the amylopectin of the 203MH plants compared to the amylopectin of wild type plants and also to 072VL plants. If the mean is calculated from the relative proportions of the side chains having a DP of 26 to DP 31, the following values are obtained (Tab. 3):

TABLE 3

| | Desi Mix | 072VL036 | 203MH10 | 203MH61 | 203MH80 |
|---|---|---|---|---|---|
| mean of the relative proportions of DP 26 to DP 31 | 1.24 | 1.85 | 3.43 | 3.43 | 4.15 |

TABLE 3-continued

|  | Desi Mix | 072VL036 | 203MH10 | 203MH61 | 203MH80 |
|---|---|---|---|---|---|
| change in % compared to Desi Mix (=100%) | 100 | 149 | 276 | 276 | 335 |

The amylopectin of 203MH plants is characterised by an increased proportion of side chains having a DP of 26 to DP 31 compared to amylopectin of wild type plants and also of 072VL plants.

Figure 2:
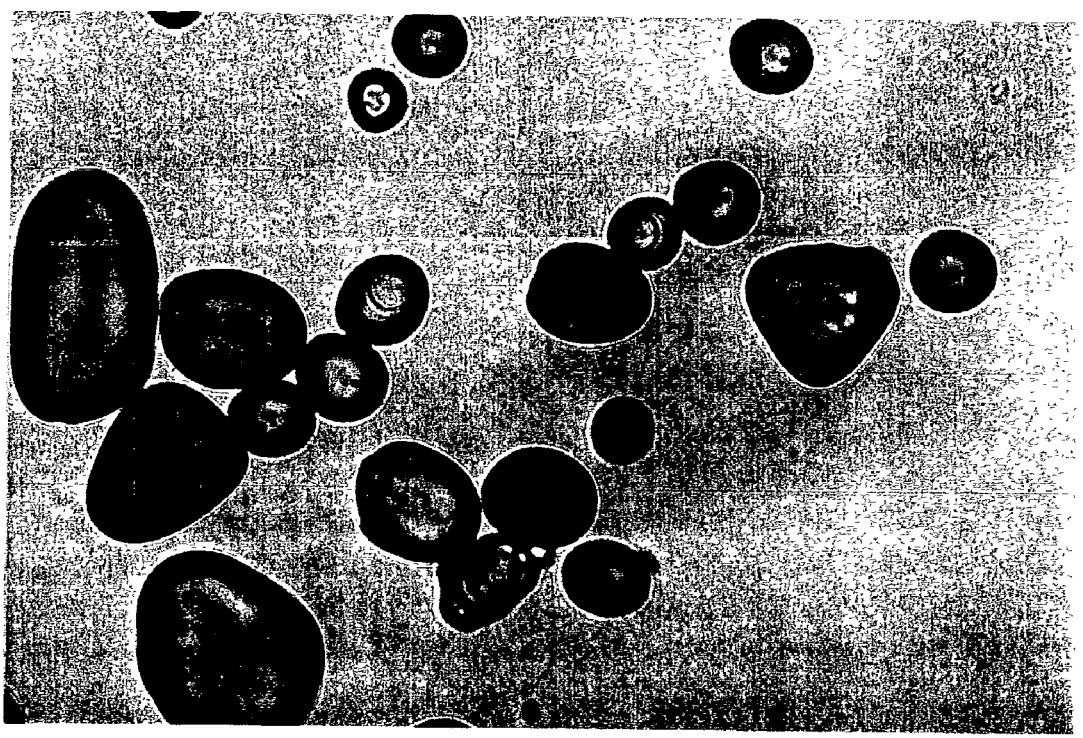
FIG. 2: Light-microscopic view of starch granules of wild type potato plants.

Furthermore, the morphology of the starch granules was examined:

The surface of the starch granules of wild type plants appears smooth under the light microscope. The form of the granules is round to oval, no "internal structures" being noticeable. Moreover, a uniform distribution of the different granule sizes can be seen (cf. FIG. 2).

Figure 3:
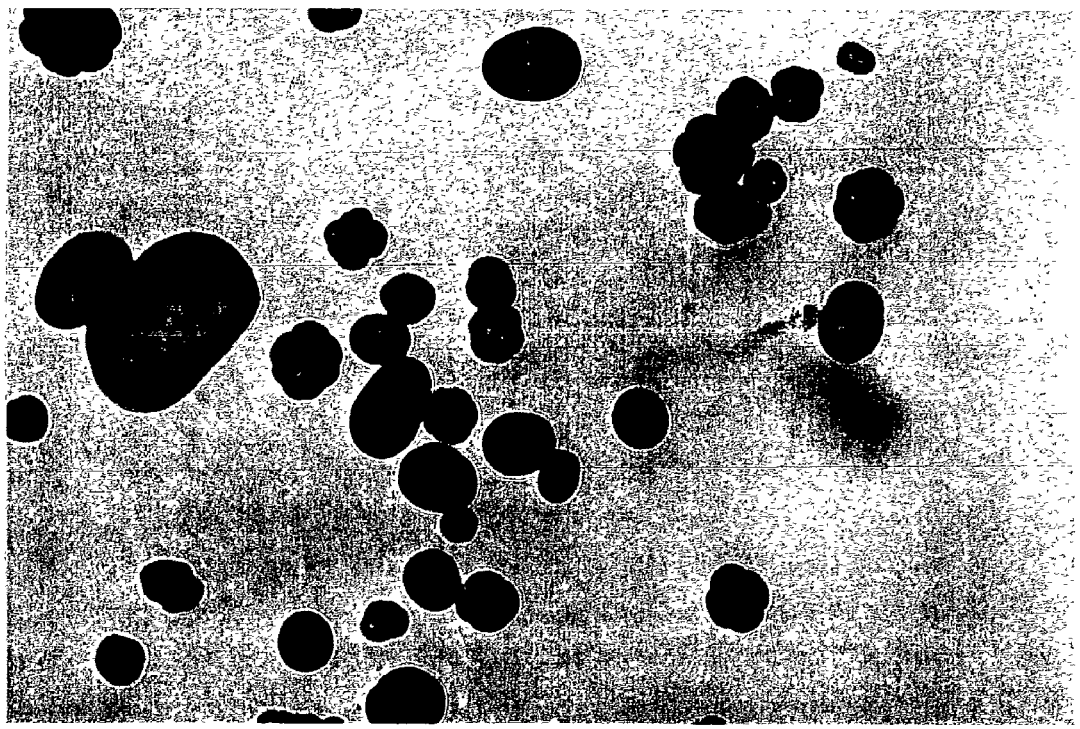
FIG. 3: Light-microscopic view of starch granules of 072VL036 potato plants having a reduced gene expression of the R1 and BEI gene.

Starch granules of 072VL036 plants (FIG. 3) have a very heterogeneous appearance. Only some granules appear smooth, others have grooves, some show "bunch-of-grapes-like agglomerations". Other granules have cross-recess-like structures. The spectrum of granule sizes is broad, smaller granules making up a greater proportion than is the case with starch granules of wild type plants.

Figure 4:
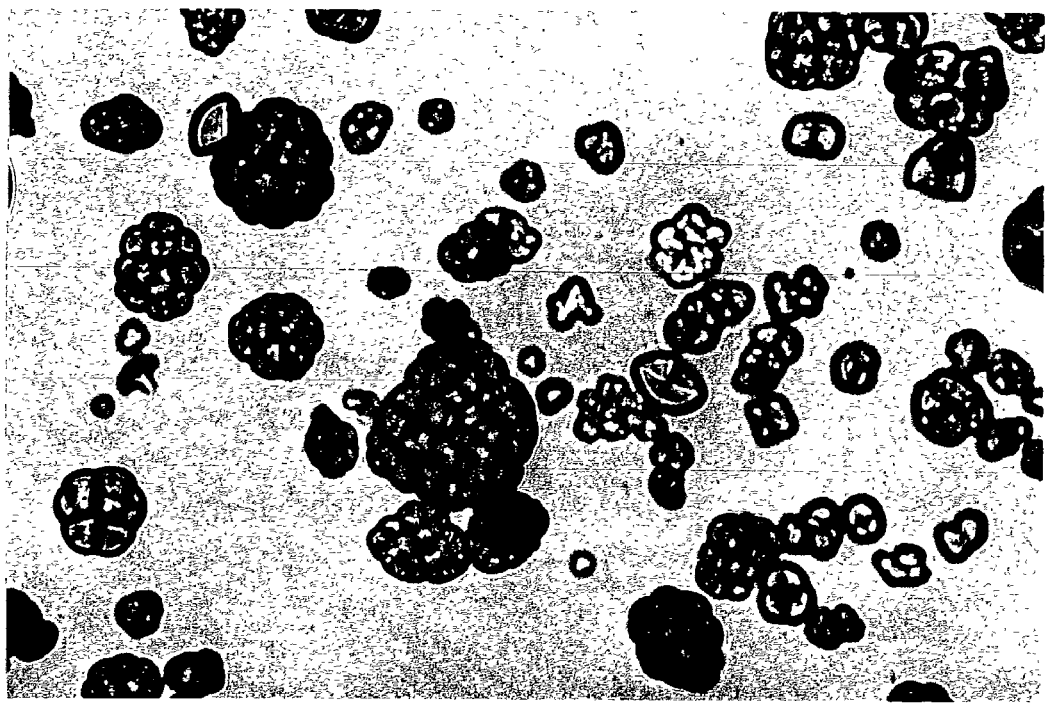
FIG. 4: Light-microscopic view of starch granules of 203MH010 potato plants according to the invention.

The morphology of the granules of the line 203MH010 (FIG. 4), too, is heterogeneous, though less apparent than in 072VL036 plants. The surface of almost all granules has grooves, most of the granules show bunch-of-grapes-like agglomerations. Sometimes, particles can be seen which look like fragments of these agglomerated structures. The size distribution is relatively broad, smaller granules dominate though.

Furthermore, the granule size was determined using a photo sedimentometer of the type "Lumosed" by Retsch GmbH, Germany.

The average granule size of both untreated starch samples and samples which, prior to the granule size determination, were subjected to an overall 3-minute mechanical fragmentation was measured (for conduction see above) (Tab. 4).

In addition, the proportion of starch granules having a size of <20 μm was determined (Tab. 5)

TABLE 4

| | average granule size [μm] | |
|---|---|---|
| sample | untreated | mechan. fragmentation |
| Wt | 23.86 | 22.27 |
| 072VL036 | 16.88 | 16.78 |
| 203MH010 | 14.78 | 11.31 |
| 203MH066 | 14.59 | 11.82 |
| 203MH080 | 14.31 | 12.14 |

TABLE 5

| | Proportion of granules < 20 μm [%] | |
|---|---|---|
| sample | untreated | mechan. fragmentation |
| Wt | 51.7 | 49.3 |
| 072VL036 | 69.7 | 69.9 |
| 203MH010 | 85.8 | 92.9 |
| 203MH066 | 83.7 | 90.6 |
| 203MH080 | 88.4 | 91.1 |

The results show that both the average granule size and the proportion in percent of starch granules <20 μm of the starches of the invention differ significantly from wild type starches as well as from starches derived from 072VL036 plants.

After mechanical fragmentation of the starches, these differences are even more significant than without mechanical treatment.

---

The invention claimed is:

1. A transgenic plant cell which has been genetically modified, the plant cell comprising:
   a) in an antisense orientation relative to a promoter, a nucleic acid sequence of at least 500 nucleotides that hybridizes under high stringency conditions to a gene encoding an endogenous starch phosphorylase (R1) protein and that leads to the reduction, compared to the non-genetically modified plant cell, of the expression of one or more endogenous starch phosphorylase (R1) proteins;
   b) in an antisense orientation relative to a promoter, a nucleic acid sequence of at least 500 nucleotides that hybridizes under high stringency conditions to a gene encoding an endogenous branching enzyme I (BEI) protein and that leads to the reduction, compared to the non-genetically modified plant cell, of the expression of one or more endogenous branching enzyme I (BEI) proteins; and
   c) in an antisense orientation relative to a promoter, a nucleic acid sequence of at least 500 nucleotides that hybridizes under high stringency conditions to a gene encoding an endogenous branching enzyme II (BEII) protein and that leads to the reduction, compared to the non-genetically modified plant cell, of the expression of one or more endogenous branching enzyme II (BEII) proteins.

2. A transgenic plant cell comprising at least one nucleic acid molecule comprising:
   a) a nucleic acid sequence comprising at least 500 nucleotides of a starch phosphorylase (R1) gene operably linked to a promoter in an antisense orientation leading to reduced expression of an endogenous gene encoding a starch phosphorylase (R1) protein compared to expression in the non-transgenic plant cell;
   b) a nucleic acid sequence comprising at least 500 nucleotides of a branching enzyme I (BEI) gene operably linked to a promoter in an antisense orientation leading to reduced expression of an endogenous gene encoding a branching enzyme I (BEI) protein compared to expression in the non-transgenic plant cell; and
   c) a nucleic acid sequence comprising at least 500 nucleotides of a branching enzyme II (BEII) gene operably linked to a promoter in an antisense orientation leading to reduced expression of an endogenous gene encoding a branching enzyme II (BEII) protein compared to expression in the non-transgenic plant cell.

3. The transgenic plant cell according to claim 1 or 2 which synthesizes a modified starch.

4. The transgenic plant cell according to claim 3, wherein the modified starch has an amylose content of at least 75% and a reduced phosphate content compared to starch from a non-transgenic plant cell.

5. The transgenic plant cell according to claim 3, wherein the modified starch has a modified distribution of the side chains.

6. A transgenic plant comprising the transgenic plant cell according to claim 1 or 2.

7. A method for producing a transgenic plant cell that synthesizes a modified starch, comprising the step of introducing into a plant cell at least one nucleic acid molecule, wherein said at least one nucleic acid molecule comprises:
   a) a nucleic acid sequence comprising at least 500 nucleotides of a starch phosphorylase (R1) gene operably linked to a promoter in an antisense orientation leading to reduced expression of an endogenous gene encoding a starch phosphorylase (R1) protein compared to expression in the non-transgenic plant cell;
   b) a nucleic acid sequence comprising at least 500 nucleotides of a branching enzyme I (BEI) gene operably linked to a promoter in an antisense orientation leading to reduced expression of an endogenous gene encoding a branching enzyme I (BEI) protein compared to expression in the non-transgenic plant cell; and
   c) a nucleic acid sequence comprising at least 500 nucleotides of a branching enzyme II (BEII) gene operably linked to a promoter in an antisense orientation leading to reduced expression of an endogenous gene encoding a branching enzyme II (BEII) protein compared to expression in the non-transgenic plant cell;
   thereby producing the transgenic plant cell that synthesizes a modified starch.

8. The method of claim 7, wherein the modified starch has an amylose content of at least 75% and a reduced phosphate content in comparison with starch from a non-transgenic plant cell.

9. A method for producing a transgenic plant that synthesizes a modified starch comprising the step of
   regenerating a plant from a plant cell produced according to the method of claim 7,
   thereby producing the transgenic plant that synthesizes a modified starch.

10. The method according to claim 9, wherein the modified starch has an amylose content of at least 75% and a reduced phosphate content in comparison with starch from a non-transgenic plant.

11. A transgenic plant obtained by the method according to claim 9 or 10.

12. The transgenic plant according to claim 6 which is a starch-storing plant.

13. The transgenic plant according to claim 12 which is a potato plant.

14. Propagation material of the plant according to claim 6, wherein the propagation material comprises the transgenic plant cell.

15. A nucleic acid molecule comprising:
   a) a nucleic acid sequence comprising at least 500 nucleotides of a starch phosphorylase (R1) gene operably linked to a promoter in an antisense orientation, which when expressed in a plant cell leads to reduced expression of an endogenous gene encoding a starch phosphorylase (R1) protein compared to a the non-transformed plant cell;
   b) a nucleic acid sequence comprising at least 500 nucleotides of a branching enzyme I (BEI) gene operably linked to a promoter in an antisense orientation, which when expressed in a plant cell leads to reduced expression of an endogenous gene encoding a branching enzyme I (BEI) protein compared to the non-transformed plant cell; and
   c) a nucleic acid sequence comprising at least 500 nucleotides of a branching enzyme II (BEII) gene operably linked to a promoter in an antisense orientation, which when expressed in a plant cell leads to reduced expression of an endogenous gene encoding a branching enzyme II (BEII) protein compared to the non-transformed plant cell.

16. A host cell comprising the nucleic acid molecule according to claim 15.

17. The host cell according to claim 16, wherein the cell is a plant cell.

18. The transgenic plant according to claim 11 which is a starch-storing plant.

19. The transgenic plant according to claim 18 which is a potato plant.

20. Propagation material of the plant according to claim 11, wherein the propagation material comprises the transgenic plant cell.

* * * * *